United States Patent [19]
Haake

[11] Patent Number: 5,989,547
[45] Date of Patent: Nov. 23, 1999

[54] LEPTOSPIRAL OUTER MEMBRANE PROTEINS

[75] Inventor: David A. Haake, Culver City, Calif.

[73] Assignee: University of California, Los Angeles, Calif.

[21] Appl. No.: 08/786,074

[22] Filed: Jan. 21, 1997

Related U.S. Application Data

[60] Provisional application No. 60/010,316, Jan. 22, 1996.
[51] Int. Cl.$^6$ .......................... A61K 39/00; A61K 39/02; C07K 1/00; C12P 21/04
[52] U.S. Cl. ...................... 424/184.1; 424/190.1; 424/262.1; 424/234.1; 424/266.1; 530/300; 530/350; 530/359; 435/71.1
[58] Field of Search ............................. 424/234.1, 262.1, 424/190.1, 184.1, 266.1; 530/300, 350, 359; 435/71.1

[56] References Cited

U.S. PATENT DOCUMENTS

| | | |
|---|---|---|
| 5,558,993 | 9/1996 | Champion et al. . |
| 5,643,754 | 7/1997 | Haake . |
| 5,658,757 | 8/1997 | Haake et al. . |
| 5,705,332 | 1/1998 | Roll . |
| 5,730,969 | 3/1998 | Hora et al. . |
| 5,753,459 | 5/1998 | Blanco et al. . |
| 5,824,321 | 10/1998 | Haake . |
| 5,837,263 | 11/1998 | Haake . |
| 5,854,395 | 12/1998 | Champion et al. . |

FOREIGN PATENT DOCUMENTS

| | | |
|---|---|---|
| WO 95/32220 | 11/1995 | WIPO . |
| WO 96/36355 | 11/1996 | WIPO . |

OTHER PUBLICATIONS

Champion et al, Infect. Imm. 62(7): 2653–2661, Jul. 1994.
Brown et al, Infect & Imm. 59(5): 1772–1777, May 1991.
Alves, Selmo Fernandes, "Immunochemical and Protection Studies Analysis of Leptospira", Dissertation, University of California, Davis, approved by thesis committee in 1993 (Title Page, Table of Contents, Table 2).
Auran, et al., "Isolation of the Outer Sheath of Leptospira and Its Immunogenic Properties in Hamsters", *Infect. Immun.*, 5:968–975 (1972).
Bey, R. F., et al., "Immunogrnicity of Whole Cell and Outer Envelope Leptospiral Vaccines in Hamsters", *Infect. Immun.*, 10:1051–1056 (1974).
Blanco, et al., "Isolation of the Outer Membranes from *Treponema pallidum* and *Treponema vincentii*", *J. Bacteriol.*, 176:6088–6099 (1994).
Bolin, C. A., et al., "Effect of vaccination with a monovalent *Leptospira interrogans* serovar hardjo type hardjo–bovis vaccine on type hardjo–bovis infection of cattle",*Am. J. Vet. Res.*, 52:1639–1643 (1991).
Cunningham, et al., "Selective Release of the *Treponema pallidum* Outer Membrane and Associated Polypeptides with Triton X–114", *J. Bacteriol.*, 170:5789–5796 (1988).

Haake, D. A., et al., "Changes in the surface of *Leptospira interrogans* Serovar grippotyphosa during In Vitro Cultivation", *Infect. Immun.*, 59(3): 1131–40 (1991).
Haake, D. A., et al., "Molecular Cloning and Sequence Analysis of the Gene Encoding OmpL1, a Transmembrane Outer Membrane Protein of Pathogenic Leptospira spp,",*J. Bacteriol.*, 175:4225–4234 (1993).
Holt, S. C., "Anatomy and Chemistry of Spirochetes", *Microbiol. Rev.*, 42:114–160 (1978).
Nicholson, et al., "Outer membrane proteins of three pathogenic Leptospira species", *Veterinary Microbiology*, 36:123–138 (1993).
Nunes–Edwards, P. L., et al., "Identification and Characterization of the Protein Antigens of *Leptospira interrogans* serovar hardjo", *Infect. Immun.*, 48:492–497(1985).
Osborn, et al., "Mechanism of Assemblly of the Outer Membrane of *Salmonella typhimurium*", *J. Biol. Chem.*, 247:3962–3972 (1972).
Penn, et al., "The Outer Membrane of *Treponema pallidum*: Biological Significance and Biochemical Properties", *J. Gen. Microbiol.*, 131:2349–2357 (1985).
Radolf, et al., "Characterization of Outer Membranes Isolated from *Borrelia burgdorferi*, the Lyme Disease Spirochete", *Infect. Immun.*, 63:2154–2163 (1995).
Radolf, et al., "Characterization of Outer Membranes Isolated from *Treponema pallidum*, the Syphilis Spirochete", *Infect. Immun.*, 63:4244–4252 (1995).
Shang, E. S. et al., "The Rare Outer Membrane Protein, OmpL1, of Pathogenic Leptospira Species Is a Heat–Modifiable Porin", *Infect. Immun.* 63(8):3174–3181 (1995).
Shang, E. S., et al., "Molecular Cloning and Sequence Analysis of the Gene Encoding LipL41, a Surface–Exposed Lipoprotein of Pathogenic Leptospira Species", *Infect. Immun.*, 64:2322–2330 (1996).
Skare, et al., "Virulent Strain Associated Outer Membrane Proteins of *Borrelia burgdorferi*", *J. Clin. Invest.*, 96:2380–2392 (1995).
Stamm, et al., "Changes in the Cell Surface Properties of *Treponema pallidum* that Occur During In Vitro Incubation of Freshly Extracted Organisms", *Infect. Immun.*, 5:2255–261 (1987).

(List continued on next page.)

*Primary Examiner*—Nita Minnifield
*Attorney, Agent, or Firm*—Gray, Cary, Ware & Freidenrich, LLP; Lisa A. Haile

[57] ABSTRACT

This invention presents antigenic preparations of Leptospira species outer membrane proteins and their immunogenic fragments which are useful for inducing immune response in animals, e.g., for use as vaccines against diseases caused by leptospirosis. Also presented are methods and kits for diagnosing leptospirosis by detecting the presence of these proteins, their immunogenic fragments, antibodies to these proteins or their fragments, or polynucleotides which encode or are translatable into these proteins or their fragments. Further disclosed are methods for isolating these proteins.

10 Claims, 15 Drawing Sheets

OTHER PUBLICATIONS

Weigel, L. M., et al., "The 47–kDa major lipoprotein immunogen of *Treponema palldium* is a penicillin–binding protein with carboxypeptidase activity", *Proc. Natl. Acad. Sci. USA*, 91:11611–11615 (1994).

Weigel, L. M., et al., "Digoxigenin–Ampicillin Conjugate for Detection of Penicillin–Binding Proteins by Chemiluminescence", *Antimicrob. Agents Chemother.*, 38(2):330–336 (1994).

Yang, N.–S. et al., Gene Therapy via Particle Bombardment: Applications of the Accell Gene Gun, in *Gene Therapeutics: Methods and Applications of Direct Gene Transfer*, Wolff, J. A., ed., Birkhauser, USA (1994).

Zuerner, et al., "Characterization of outer membrane and secreted protens of *Leptospira interrogans* serovar pomona", *Microbial Pathogenesis*, 10:311–322 (1991).

LEPTOSPIRAL OUTER MEMBRANE PROTEINS

This application claims priority to provisional application Ser. 60/010316 filed Jan. 22, 1996, now abandoned.

This invention was made with Government support through funding from the Veterans' Administration Medical Research Funds. The Government has certain rights in this invention.

TECHNICAL FIELD OF THE INVENTION

This invention relates generally to an antigenic preparation and particularly to Leptospira species outer membrane proteins which are used to induce a protective immune response in animals. Such proteins can be used immunologically as vaccines for leptospirosis caused by this organism. Alternatively, diagnosis of leptospirosis can be performed by detecting the presence of the proteins, antibodies to the proteins, or polynucleotides which encode the proteins. Also disclosed are methods for isolating proteins of the outer membranes of microorganisms, e.g. spirochetes such as those of the Leptospira species.

BACKGROUND OF THE INVENTION

Leptospirosis is an important, global human and veterinary health problem. It is a widespread zoonotic disease caused by pathogenic strains of Leptospira species which are capable of infecting most mammalian species. Infection occurs either through direct contact with an infected animal or indirect contact with contaminated soil or water. In livestock, the disease causes economic losses due to abortion, stillbirth, infertility, decreased milk production, and death.

Efforts to control leptospirosis have been hampered because virulent leptospires have the capacity for both long-term survival in the environment as well as persistent infection and shedding by wildlife and livestock. Currently available leptospiral vaccines produce short-term immunity and do not provide cross-protection against many of the 170 serovars of pathogenic Leptospira species {Thiermann, et al., *J. Am. Vet. Med. Assoc.*, 184:722 (1984)}. These vaccines consist of inactivated whole organisms or outer envelope preparations which produce seroreactivity as determined by microscopic agglutination of intact organisms. The nature of the protective immunogens in these vaccine preparations has not been conclusively elucidated, although several lines of evidence suggest that lipopolysaccharide-like substance ("LLS") may confer a degree of protection. Commercially available vaccines, which consist of heat or formalin-killed leptospires, produce incomplete or only short-term immunity, requiring their administration annually or semiannually. In the case of *L. interrogans* serovar *hardjo*, the common bovine pathogen in North America, vaccines prepared in this way are ineffective {Bolin, C. A., et al., *Am. J. Vet. Res.*, 50:161–165 (1989) and Bolin, C. A., et al., *Am. J. Vet. Res.*, 50:2004–2008 (1989)}. Thus there is an important need for development of an improved leptospiral vaccine.

The pathogenesis of leptospirosis is similar to that of other spirochetal diseases, including syphilis (caused by *Treponema pallidum*) and Lyme borreliosis (caused by *Borrelia burgdorferi*). Both syphilis and Lyme borreliosis are characterized by widespread dissemination early in the course of disease, including invasion of the central nervous system. Leptospira species share this ability with other pathogenic spirochetes such that meningitis is a common manifestation of leptospirosis. Another feature of spirochetal infections is the ability to persist chronically in the host, as manifested in cases of tertiary syphilis and chronic Lyme arthritis.

Identification of outer membrane ("OM") components is essential in the development of protective immunogens for spirochetal diseases. There are at least two classes of leptospiral outer membrane proteins ("OMPs"). One class of leptospiral OMPs are the transmembrane proteins, such as the porin OmpL1 and the TonB-dependent OmpL2, that are produced in small amounts by pathogenic Leptospira species {Haake, D. A., et al., *J. Bacteriol.*, 175:4225–4234 (1993); Haake, D. A., et al.}. Transmembrane OMPs are distinguished from other membrane proteins structurally by the fact that they contain beta-sheet membrane-spanning regions. They are also functionally unique in that they create channels for transport of nutrients across the outer membrane.

A second class of leptospiral OMPs are the lipoproteins, which are produced by Leptospira species in generous amounts. Lipoproteins are anchored to membranes by fatty acids attached to their amino-terminal cysteine. Both the outer membrane and cytoplasmic membrane contain lipoproteins, and the signal(s) by which lipoproteins are translocated to the outer membrane are not known. Therefore, in order to define a lipoprotein as an OMP, it must be shown to be a component of isolated leptospiral OM. Several Triton X-114 detergent phase lipoproteins have been identified, including LipL36 (also referred to as "LipL1") and LipL41 (also referred to as "LipL2"). LipL1 and LipL2 are described in Shang, E. S., et al., "Molecular Cloning and Sequence Analysis of the Genes Encoding Two Leptospiral Lipoproteins, LipL1 and LipL2", Abstract No. D-2, in Abstracts of the Annual Meeting of the American Society for Microbiology, May 21–25, 1995, p. 249 (American Society for Microbiology, Washington, DC, 1995), this reference is herein incorporated by reference in its entirety. The Triton-extractable 32-kDa major outer membrane protein is probably also a lipoprotein {Zuerner, et al., *Microbial Pathogenesis*, 10:311–322 (1991)}. However, lacking a carefully defined technique for isolating the leptospiral OM, it was not possible to determine to what extent these lipoproteins are found in the OM, nor to identify additional components of the leptospiral OM.

Development of techniques for isolation of the OM from Leptospira species and other spirochetes has been difficult because of their unique architecture {Holt, S. C., *Microbiol. Rev.*, 42:114–160 (1978)}. Like enteric gram-negative bacteria, spirochetes have both an outer membrane and a & cytoplasmic membrane, separated by a periplasmic space. However, spirochetal architecture differs significantly from that of gram-negative bacteria in that the peptidoglycan cell wall of spirochetes is associated with the cytoplasmic membrane rather than the outer membrane. For this reason, the spirochetal outer membrane is extremely labile and difficult to isolate from components of the underlying cell wall and cytoplasmic membrane which together constitute the protoplasmic cylinder ("PC").

A number of approaches have been used in the isolation of the leptospiral outer membrane {Auran, et al., *Infect. Immun.*, 5:968–975 (1972); Nunes-Edwards, et al., *Infect. Immun.*, 48:492–497(1985); Nicholson, et al., *Veterinary Microbiology*, 36:123–138 (1993)}. These studies did not take into account spirochetal outer membrane fragility and the lack of OM selectivity of ionic or nonionic detergents {Penn, et al., *J. Gen. Microbiol.*, 131:2349 (1985); Stamm, et al., *Infect. Immun.*, 55:2255 (1987); and Cunningham, et al., *J. Bacteriol.*, 170:5789 (1988)}. Notably lacking from these reports are controls to assess contamination of the OM fraction with PC components. Recently, spirochetal OM isolation has been advanced by developments in three areas. Firstly, specific OM markers such as porins (e.g. OmpL1) have been identified, allowing assessment of efficiency of OM release. Secondly, techniques have been developed for assessing the degree of contamination with PC components. Thirdly, new techniques involving hypotonic citrate and hypertonic sucrose have been found to be of use in the isolation of the OM of *Treponema* species {Blanco, et al.,*J. Bacteriol.*, 176:6088–6099 (1994); Radolf, et al., *Infect. Immun.*, 63:2154–2163 (1995)} and *B. burgdorferi* {Skare, et al., *J. Clin. Invest.*, 96:2380–2392 (1995); Radolf, et al., *Infect. Immun.*, 63:4244–4252 (1995)}. Without modification, these techniques did not facilitate isolation of the leptospiral OM.

SUMMARY OF THE INVENTION

The present invention presents novel leptospiral outer membrane proteins. Also disclosed are methods for purifying these proteins from Leptospira species. In particular, thirteen OM proteins are disclosed, the molecular masses of these proteins are about 22-, 24-, 30-, 37-, 46-, 51-, 56-, 67-, 70-, 74-, 93-, 101-, and 127-kDa, respectively. These proteins, their immunogenic fragments, and antibodies capable of binding to them, are useful for inducing an immune response to pathogenic Leptospira species as well as providing a diagnostic target for leptospirosis. Also disclosed are three methods useful for isolating outer membrane proteins of microorganisms such as spirochetes, particularly for isolating leptospiral outer membrane in the form of membrane vesicles.

DETAILED DESCRIPTION OF THE INVENTION

Figure 1:
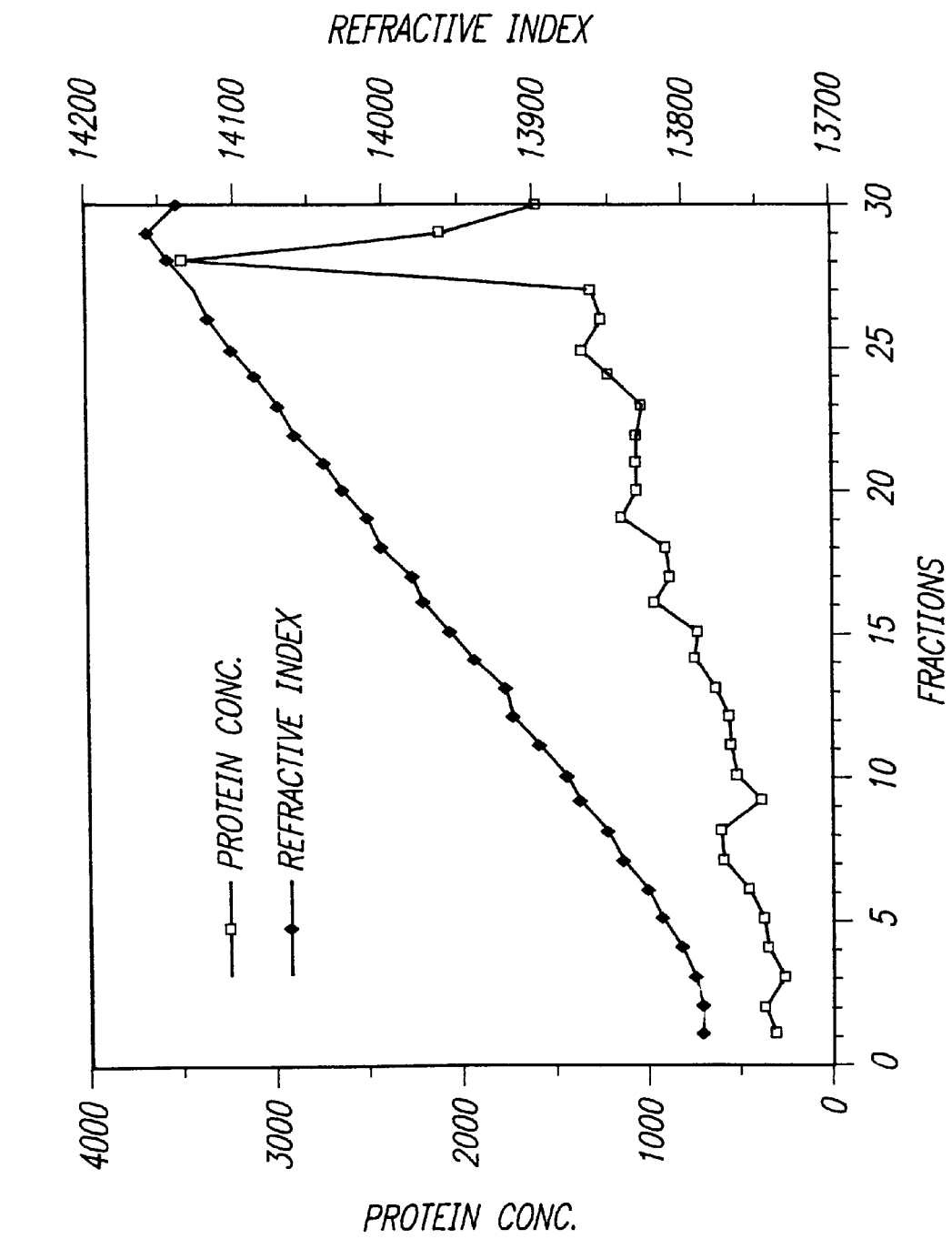
FIG. 1 presents sucrose gradient fractionation of *L. kirschneri* treated with Citrate/NaCl. Fractions were tested for refractive index and protein concentration.

The present invention presents novel leptospiral outer membrane proteins. Also disclosed are methods for purifying these proteins from Leptospira species. In particular, thirteen OM proteins are disclosed, the molecular masses of these proteins are about 22-, 24-, 30-, 37-, 46-, 51-, 56-, 67-, 70-, 74-, 93-, 101-, and 127-kDa, respectively. These proteins, their immunogenic fragments, and antibodies capable of binding to them, are useful for inducing an immune response to pathogenic Leptospira species as well as providing a diagnostic target for leptospirosis. Also disclosed are three methods useful for isolating outer membrane proteins of microorganisms such as spirochetes, particularly for isolating leptospiral outer membrane in the form of membrane vesicles.

By taking into account the unique features of leptospiral architecture, the present invention presents successful modification of the citrate, hypertonic sucrose, and French pressure cell techniques for use in the isolation of leptospiral OM.

The standard method for isolation of the leptospiral outer membrane involves treatment of Leptospira species with hypertonic saline, resulting in salt-altered cells ("SACs") in which the outer membrane is dissociated from the underlying protoplasmic cylinder, followed by release of the outer membrane with the ionic detergent sodium dodecyl sulfate ("SDS") {Auran, et al., *Infect. Immun.*, 5:968–975 (1972); Nunes-Edwards, et al., *Infect. Immun.*, 48:492–497 (1985)}. Another study applied a technique developed for isolation of the *Haemophilus influenzae* outer membrane involving sonication and sodium-N-lauroylsarcosinate {Nicholson, et al., *Veterinary Microbiology*, 36:123–138 (1993)}. Disruption of organisms using sonication or a French Press can result in formation of outer membrane-cytoplasmic membrane hybrids {Osborn, et al., *J. Biol. Chem.*, 247:3962–3972 (1972)}. Both of these approaches result in recovery of membrane vesicles containing leptospiral lipopolysaccharide ("LPS"). However, in neither case was an attempt made to evaluate the selectivity of these detergent-based approaches by assessing contamination of the outer membrane fraction with PC components. Due to the unique architecture of spirochetes, and the fragility of the outer membrane, it cannot be assumed that there is differential solubility of leptospiral membranes to SDS or sodium-N-lauroylsarcosinate.

Previously, the use of Triton X-114 in solubilization of the leptospiral outer membrane were examined {Haake, et al., *Infect. Immun.*, 59:1131–1140 (1991); Zuerner, et al., *Microbial Pathogenesis*, 10:311–322 (1991)}. This approach appears to be somewhat selective based upon analysis of the Triton X-114 detergent phase for contamination with flagella and penicillin-binding proteins {Haake, et al., *Infect. Immun.*, 59:1131–1140 (1991)}. However, some cytoplasmic membrane proteins may be more susceptible to solubilization by Triton X-114 than others. For example, the nonionic detergent Triton X-114 solubilizes the TpN47 lipoprotein of *Treponema pallidum* which has been shown to be a cell wall associated penicillin-binding protein {Weigel, L. M., et al., *Proc. Natl. Acad. Sci. USA*, 91:11611–11615 (1994)}. In addition, generation of the Triton X-114 detergent phase may result in loss of certain leptospiral OMPs. For example, proteolytic degradation of the leptospiral 32-kDa major outer membrane protein ("MOMP") has been observed during Triton X-114 phase partitioning {Zuerner, et al., *Microbial Pathogenesis*, 10:311–322 (1991)}.

Spirochetal OM isolation has been advanced by developments in three areas. Firstly, specific OM markers such as porins (e.g. OmpL1) have been identified, allowing assessment of efficiency of OM release. Secondly, techniques have been developed for assessing the degree of contamination with PC components. Thirdly, new techniques have been developed for isolation of the spirochetal OM that do not involve the use of detergents or mechanical disruption. It was discovered that exposure of *T. pallidum* and *T. vincentii* to a hypotonic sodium citrate buffer, pH 3.2 resulted in the release of the outer membrane as unilamellar vesicles {Blanco, et aL, *J. Bacteriol.*, 176:6088–6099 (1994)}. Once released, the outer membrane vesicles could then be isolated by sucrose gradient centrifugation. The hypotonic citrate technique that was applied to the *T. pallidum* has also been applied to the isolation of the *Borrelia burgdorferi* outer membrane {Skare, et al., *J. Clin Invest.*, 96:2380–2392 (1995)}. The second new technique involves the use of hypertonic sucrose to release *T. pallidum* and *B. burgdorferi* OMs {Radolf, et al., *Infect. Immun.*, 63:2154–2163 (1995); Radolf, et al., *Infect. Immun.*, 63:4244–4252 (1995)}. When these techniques were applied without modification, they did not facilitate isolation of the leptospiral OM. However, by taking into account the unique features of leptospiral architecture, the present invention was successful in modifying the citrate and hypertonic sucrose techniques for use in the isolation of leptospiral OM.

The OM proteins may be isolated from Leptospira species by the methods of the present invention. For the purpose of convenience, the discussion uses leptospiral OM proteins as examples. However, one skilled in the art would realize that the discussion is also applicable to OM proteins obtained from other microorganisms such as spirochetes using the methods of the present invention with the appropriate modifications known in the art for the particular organisms of interest.

In addition to the thirteen OM proteins disclosed in the "EXAMPLE" section, below, within the definition of the term "OM proteins" are also other OM proteins which are obtainable by the isolation methods disclosed in the present invention, preferably the methods disclosed in the "EXAMPLE" section below.

The present invention discloses three isolation methods. The first two use both hypertonic sucrose and hypotonic citrate buffer to release the leptospiral outer membrane from the protoplasmic cylinder. The third technique for isolation of the leptospiral outer membrane utilizes the French pressure cell, at a pressure sufficient to release the OM, most preferably at about 12,000 lb/in$^2$. The first two isolation methods of the present invention preferably have the following combination of features which make them different from the prior art. The methods do not use detergent nor disrupt the organism (e.g. by sonication), even though detergent treatment and disruption of the organism are traditionally used for the extraction of outer membrane proteins. The present methods also use outer membrane markers (such as antisera to LipL36, LipL41, and OmpL1) and markers for PC (such as NADH oxidase, flagella and GroEL) to follow the recovery of the outer membrane proteins. Preferably, the methods modified the prior art by adding NaCl to the citrate or sucrose isolation techniques for the membrane proteins of spirochetes. Most preferably, the methods are used to isolate the leptospiral outer membrane as membrane vesicles. The membrane vesicles can then be isolated, e.g. by ultracentrifugation, such as by sucrose gradient ultracentrifugation. In both methods, preferably about 1 M of NaCl is used. In the method using citrate and NaCl, preferably the citrate buffer is used at about 25 mM and about pH 3.2. In the method using hypertonic sucrose and NaCl, the hypertonic sucrose is preferably in about 10 mM Tris at about pH 9. In place of NaCl, another chemical may be used if the chemical would disrupt the electrostatic interaction between the PC and the outer membrane such that the PC is not released until the citrate buffer or hypertonic sucrose is added.

In the preferred embodiment of the first two isolation methods, the leptospiral outer membrane ("OM") was isolated in the form of membrane vesicles by the first two techniques. *Leptospira kirschneri* were incubated in 1.0 M NaCl containing either citrate buffer (25 mM pH 3.2) or hypertonic sucrose (10 mM Tris pH 9). The OM was separated from the PC by sucrose density gradient ultracentrifugation. Both techniques facilitated release from the OM from the PC as indicated by analysis of PC markers NADH oxidase, flagella, and the 60-kDa heat shock protein ("GroEL"). However, refractive index analysis indicated that there was better separation of OM from PC components with citrate buffer than with hypertonic sucrose. On the other hand, treatment with hypertonic sucrose resulted in better recovery of known OM components, LPS and OmpL1, than treatment with citrate buffer. The OM fractions contained leptospiral LPS, the porin OmpL1, the lipoproteins LipL41 and LipL36, a 32-kDa major outer membrane protein, as well as a number of OM proteins with molecular masses of about 22-, 24-, 37-, 46-51-, 56-, 67-, 70-, 74-, 93-, 101-, and 127-kDa. The use of membrane-specific markers in OM isolation techniques facilitates an accurate description of the leptospiral OM and its components.

The third method, the French pressure technique of leptospiral outer membrane isolation has an advantage over the hypertonic sucrose and hypotonic citrate buffer techniques because it uses mechanical disruption to more efficiently release the outer membrane in the form of membrane vesicles.

The present invention also presents the use of a digoxigenin-ampicillin conjugate, a sensitive probe for penicillin-binding proteins {Weigel, L. M., et al., *Antimicrob. Agents Chemother.*, 38(2): 330–336 (1994)}, which are located exclusively in the cytoplasmic membrane. This conjugate may be used in combination with any isolation technique, including the three isolation techniques disclosed herein. In the following EXAMPLE 2, the digoxigenin-ampicillin conjugate was found to be a more sensitive probe for the cytoplasmic membrane than measures of NADH oxidase activity. In addition, penicillin-binding proteins, the targets of the digoxigenin-ampicillin conjugate, are more specific for the cytoplasmic membrane than antisera to flagella or GroEL.

Once isolated, the OM proteins can be further purified. The OM proteins may also be sequenced using methods known in the art to obtain their amino acid and nucleotide sequences, or using methods similar to those described for example, below, and in Shang, E. S., et al., "Molecular Cloning and Sequence Analysis of the Genes Encoding Two Leptospiral Lipoproteins, LipL1 and LipL2", Abstract No. D-2, in Abstracts of the Annual Meeting of the American Society for Microbiology, May 21–25, 1995, p. 249 (American Society for Microbiology, Washington, DC, 1995); Shang, E. S., et al., *Infection & Immunity*, 64: 2322–2330 (1996) and U.S. patent application Ser. No. 08/444,646 filed on May 19, 1995, "Leptospira Membrane Proteins"of Haake, D. A., et al. All these references are herein incorporated by reference in their entirety The present application claims both the native and synthetic amino acid and nucleotide sequences. Unless otherwise modified, the term "protein"as used herein encompasses both native and synthetic polypeptide and peptide. Synthetic protein includes recombinant and chemically synthesized protein. Unless otherwise indicated, the term "OM proteins" include both the native and synthetic versions of the proteins.

The term "nucleotide sequence" includes both the DNA and RNA sequences. For example, the nucleotide sequence for a particular OM protein ("OM nucleotide sequence") include the gene ("OM gene") encoding the protein, its complementary DNA, and the RNA corresponding to the foregoing; also included are messenger RNA encoding for the OM protein, its complementary RNA, and the DNA corresponding to the foregoing. Further, as used in this application the nucleotide sequences include: (1) the DNA sequences encoding the OM proteins, (2) the nucleotide sequences (which may be RNA or DNA) complementary to the foregoing sequences, (3) the corresponding RNA sequences to the DNA sequences wherein the Thymidine ("T") in the disclosed DNA sequences is replaced with Uracil ("U"), (4) nucleotide sequences wherein other nucleotides known in the art such as nucleotide analogs, replace those in the foregoing sequences, for example, 5-methylcytosine replacing cytosine, and (5) nucleotide sequences that are for example, within a 20% and preferably 10% variance to the foregoing nucleotide sequences.

Since nucleotide codons are redundant, also within the scope of this invention are equivalent nucleotide sequences which include: nucleotide sequences which code for or can be translated into the OM proteins, their protein variants, functional equivalents, or derivatives. These nucleotide sequences may also be used in the practice of the invention.

In addition to the above, OM nucleotide sequences also include: (1) nucleotide sequences that are capable of hybridizing to the coding sequences of the respective nucleotide sequences, under stringent hybridization conditions, and (2) fragments of or mutagenized nucleotide sequences of those disclosed herein which (a) encode or can be translated into proteins having substantially the same biological characteristics/activities of the respective OM proteins; or (b) are able to provoke cellular and/or humoral response in an animal vaccinated with the nucleotide sequences. Preferably, the determinative biological characteristic/ activity is the retention of at least one immunoepitope. Preferably, when used in an immunoassay for Leptospira species, these proteins are immunoreactive with antibodies directed to Leptospira species but not detectably immunoreactive with non-Leptospira species specific antibodies found in a biological sample.

As herein defined, a "biological sample" can be a biological fluid or tissue sample. Examples of a biological fluid sample include: blood, serum, plasma, tear, milk, urine, and cerebro-spinal fluid. Examples of a biological tissue sample include tissue samples from the liver and kidney and tissue of endothelial origin. A biological sample can also include feces and discharge. Thus, for example, immunohistochemical assay can be conducted on these tissue samples. Preferably, these samples are from mammals, such as humans, wild and domestic mammals. More preferably, these proteins and the immunoassays can additionally distinguish between pathogenic Leptospira species and non-pathogenic Leptospira species. Alternatively, the fragments of nucleotide sequences can be nucleotide probes of at least 10 nucleotides in length. Preferably, when used in a hybridization assay for Leptospira species, under moderate to stringent hybridization condition, these probes do not detectably hybridize to the nucleotide sequences of non-Leptospira species organisms which are found in a biological sample. Alternatively, the nucleotide sequences hybridize to at least 10 consecutive nucleotides in the coding sequences of the above listed nucleotide sequences. The nucleotide sequences include a nucleotide sequence which encodes a protein containing at least 8; more preferably, 5 to 6; and most preferably, 4 amino acids. Preferably, the protein is specific to Leptospira species or retain one or more biological functions of Leptospira species. Most preferably, these nucleotide sequences and the hybridization assays can additionally distinguish between pathogenic Leptospira species and non-pathogenic Leptospira species.

The terms "OM proteins", as used in relation to proteins include the respective proteins described in the "EXAMPLE" section, below, and outer membrane proteins obtainable by the methods of the present invention, most preferably leptospiral outer membrane proteins obtainable from the isolation methods of the "EXAMPLE" section below, and: (1) protein variants of these proteins; e.g. these protein variants may contain amino acid sequences that have for example, at least 90% or more preferably at least 95% of their amino acids matching the sequences of the OM proteins, excluding their signal peptides; (2) the functional equivalents of these proteins and their variants, respectively; and (3) the derivatives, including fragments, of the OM proteins and their variants, respectively. Preferably, when used in an immunoassay for Leptospira species, these proteins are immunoreactive (the immunoreactive OM proteins are also referred to as "OM antigens") with antibodies directed to Leptospira species but not detectably immunoreactive with non-Leptospira species specific antibodies found in a biological sample. More preferably, these proteins and the immunoassays can additionally distinguish between pathogenic Leptospira species and non-pathogenic Leptospira species. Preferably, the proteins are specific to Leptospira species or retain one or more biological functions of Leptospira species. Thus, preferably, the fragment claimed in this application contains at least one immunogenic epitope of Leptospira species and more preferably, of pathogenic Leptospira species. More preferably, the fragment is capable of being bound by polyclonal antibodies directed to Leptospira species. In the case of antibodies which recognize linear epitopes, they generally bind to epitopes defined by at least about 3 to 10 amino acids.

Alternatively or additionally, these proteins preferably possess the ability to provoke cellular and/or humoral response in an animal vaccinated with the proteins. More preferably, the cellular and/or humoral response is directed against Leptospira species, especially pathogenic Leptospira species. Most preferably, animals vaccinated with these proteins are immunized against leptospirosis or such vaccinations ameliorate the disease in infected animals. The animal is preferably a mammal. More preferably, the animal is a human or a domestic animal. Alternatively, these proteins or their amino acid sequences are preferably derivable from the membrane proteins of Leptospira species and are immunoreactive with antibodies raised against one or more OM proteins, such as the OM proteins disclosed in the "EXAMPLE" section, below.

The variants can result from, e.g. substitution, insertion, or deletion of the amino acid sequences of the OM proteins. The derivatives of the proteins and their variants, include fragments of these proteins and their immunogenic epitopes. As described above, preferably, too, each variant retains at least one immunoepitope of Leptospira species and more preferably, of pathogenic Leptospira species. Preferably the immunoepitope is specific to Leptospira species and more preferably, to pathogenic Leptospira species.

Two amino acid sequences are functionally equivalent if they have substantially the same biological activities such as the ability to provoke cellular and/or humoral response in an animal vaccinated with the proteins. The proteins may be fused to other proteins, for example, signal sequence fusions may be employed in order to more expeditiously direct the secretion of the OM proteins. Further, each of the OM proteins disclosed herein may be fused to one or more of the other OM proteins, or the LipL1 and/or LipL2 disclosed in Shang, E. S., et al., "Molecular Cloning and Sequence Analysis of the Genes Encoding Two Leptospiral Lipoproteins, LipL1 and LipL2", Abstract No. D-2, in Abstracts of the Annual Meeting of the American Society for Microbiology, May 21–25, 1995, p. 249 (American Society for Microbiology, Washington, DC, 1995); Shang, E. S., et al, Infection & Immunity, 64: 2322–2330 (1996) and U.S. patent application Ser. No. 08/444,646 filed on May 19, 1995, "Leptospira Membrane Proteins" of Haake, D. A., et al. The nucleotide sequences encoding these fusion proteins are also included in the present invention. A heterologous signal may also replace the native signal of an OM protein, and when the resulting fusion is recognized, i.e. processed and cleaved by the host cell, the OM protein is secreted. Signals are selected based on the intended host cell, and may include bacterial, yeast, insect, and viral sequences.

Substitutional variants of the proteins disclosed herein are those in which at least one residue in the disclosed sequences has been removed and a different residue inserted in its place. Preferably, the amino acid change is conservative. Thus, modifications of the OM proteins' primary amino acid sequences also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity. Such alterations which do not destroy activity do not remove the protein sequence from the definition. The following discusses some of the modifications in further detail by way of example.

Thus, glycosylation variants are included within the scope of OM proteins. They include variants completely lacking in glycosylation (unglycosylated) and variants having at least one less glycosylated site than the native form (deglycosylated) as well as variants in which the glycosylation has been changed.

The invention also includes a method of producing the membrane lipoproteins of Leptospira species using recombinant DNA techniques. Recombinant OM fusion proteins may be produced in Escherichia coli (E. coli). These proteins can be used to immunize a mammal to generate antisera. The genes for the L. kirschneri OM proteins may be cloned into a plasmid vector which is then used to transform E. coli.

After the OM proteins have been isolated, surface immuno-precipitation of the OM proteins using antiserum raised to whole L. kirschneri, may be used to generate a fraction which may be subjected to reducing SDS-polyacrylamide gel electrophoresis ("SDS-PAGE"). The electrophoresed fraction may then be transferred to a sequencing membrane and an N-terminal sequences of the proteins, may be determined. Based upon the N-terminal amino acid sequence, degenerate oligonucleotide probes may be synthesized for each of the proteins. An L. kirschneri genomic DNA library may then be probed with the oligonucleotides and inserts identified as containing the coding sequence for each of the OM proteins.

Sequence analysis of the structural genes may be conducted to determine their number of bases and amino acids. Immunoblot and immunohistochemical studies may be used to determine the correlation between leptospiral pathogenicity and reactivity with antisera to each of the OM proteins. All or some strains of pathogenic and non-pathogenic Leptospira species may be tested. These tests are preferably carried out to determine which OM proteins are specific to virulent Leptospira species such that they can be used in diagnostic tests directed to virulent Leptospira species. The sequence analysis, immunohistochemical and immunoblot studies may be conducted using methods known in the art, such as described in Shang, E. S., et al., "Molecular Cloning and Sequence Analysis of the Genes Encoding Two Leptospiral Lipoproteins, LipL1 and LipL2", Abstract No. D-2, in Abstracts of the Annual Meeting of the American Society for Microbiology, May 21–25, 1995, p. 249 (American Society for Microbiology, Washington, DC, 1995); or methods disclosed in Shang, E. S., et al., J. Infection & Immunity, 64: 2322–2330 (1996) and U.S. patent application Ser. No. 08/444,646 filed on May 19, 1995, "*Leptospira* Membrane Proteins" of Haake, D. A., et al.

The bacterial genes for the OM proteins can be derived from any strain of pathogenic Leptospira species.

The invention includes polynucleotides encoding the leptospiral OM proteins. These polynucleotides include DNA and RNA sequences which encode the protein. As discussed previously, it is understood that all polynucleotides encoding all or a portion of each of the OM proteins are also included herein, so long as they exhibit a function of the OM protein, such as the ability to induce or bind antibody. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. By using stringent hybridization conditions directed to avoid non-specific binding, it is possible, for example, to allow the autoradiographic visualization of a specific DNA clone by the hybridization of the target DNA to that single probe in the mixture which is its complete complement {Wallace, et al., *Nucleic Acid Research*, 9:879 (1981)}.

Alternatively, an expression library can be screened indirectly for the OM peptides having at least one epitope using antibodies to the OM proteins. Such antibodies can be either polyclonally or monoclonally derived and used to detect expression product indicative of the presence of OM DNA. Generally, a lambda gt11 library is constructed and screened immunologically according to the method of Huynh, et al. {in *DNA Cloning: A Practical Approach*, D. M. Glover, ed., 1:49 (1985)}.

The development of specific DNA sequences encoding the OM proteins can also be obtained by: (1) isolation of a double-stranded DNA sequence from the genomic DNA, and (2) chemical manufacture of a DNA sequence to provide the necessary codons for the polypeptide of interest.

DNA sequences encoding the OM proteins can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

The term "host cell" as used in the present invention is meant to include not only prokaryotes, but also, such eukaryotes as yeasts, filamentous fungi, as well as plant and animal cells. The term "prokaryote" is meant to include all bacteria which can be transformed with the gene for the expression of an OM protein of Leptospira species. Prokaryotic hosts may include Gram negative as well as Gram positive bacteria, such as *E. coli, S. typhimurium*, and *Bacillus subtilis.*

A recombinant DNA molecule coding for an OM protein can be used to transform a host using any of the techniques commonly known to those of ordinary skill in the art. Especially preferred is the use of a plasmid containing the OM protein coding sequence for purposes of prokaryotic transformation. Where the host is prokaryotic, such as *E. coli*, competent cells which are capable of DNA uptake can be prepared from cells harvested after exponential growth phase and subsequently treated by the $CaC_2$ method by procedures well known in the art. Alternatively, $MgC_2$ or RbC can be used. Transformation can also be performed after forming a protoplast of the host cell.

In the present invention, the OM nucleotide sequence may be inserted into a recombinant expression vector. The term "recombinant expression vector" refers to a plasmid, virus or other vehicle known in the art that has been manipulated by insertion or incorporation of OM genetic sequence. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. The transformed prokaryotic hosts can be cultured according to means known in the art to achieve optimal cell growth. Various shuttle vectors for the expression of foreign genes in yeast have been reported {Heinemann, et al., *Nature*, 340:205 (1989); Rose, et al., *Gene*, 60:237 (1987)}. Biologically functional DNA vectors capable of expression and replication in a host are known in the art. Such vectors are used to incorporate DNA sequences of the invention.

Methods for preparing fused, operably linked genes and expressing them in bacteria are known and are shown, for example, in U.S. Pat. No. 4,366,246 which is incorporated herein by reference. The genetic constructs and methods described therein can be utilized for expression of the OM proteins in prokaryotic hosts.

Examples of promoters which can be used in the invention are: rec A, trp, lac, tac, and bacteriophage lambda $p_R$, or $p_L$. Examples of plasmids which can be used in the invention are listed in Sambrook, et al. {*Molecular Cloning*, Cold Spring Harbor Laboratories, 1982}.

Antibodies provided in the present invention are immunoreactive with one or more OM proteins. These antibodies can be polyclonal antibodies or monoclonal antibodies. Polyclonal antibodies can be produced according to methods known in the art, such as, vaccinating an animal with an OM protein, collecting and purifying the animal's antisera directed against the OM protein. Monospecific polyclonal antibodies can also be produced using methods known in the art. Antibody which consists essentially of pooled monoclonal antibodies with different epitopic specificities, as well as distinct monoclonal antibody preparations are also provided. Monoclonal antibodies are made from antigen containing fragments of the protein by methods well known in the art {Kohler, et al., *Nature*, 256:495 (1975); *Current Protocols in Molecular Biology*, Ausubel, et al., ed., (1989) }. For example, monoclonal antibodies can be produced by the method of Kohler and Milstein {*Nature*, 256:495–497 (1975)} by immortalizing spleen cells from an animal inoculated with the immunogen or a fragment thereof, usually by fusion with an immortal cell line (preferably a myeloma cell line), of the same or a different species as the inoculated animal, followed by the appropriate cloning and screening steps. The antibodies may also be recombinant monoclonal antibodies produced according to the methods disclosed in Reading, U.S. Pat. No. 4,474,893, or Cabilly et al, U.S. Pat. No. 4,816,567. The antibodies may also be chemically constructed according to the method disclosed in Segel et al., U.S. Pat. No. 4,676,980.

The term antibody, or immunoglobulin, as used in this invention includes intact molecules as well as fragments thereof, such as Fab, F(ab')$_2$, Fv, and single chain antibody ("SCA") which are capable of binding an epitopic determinant on an OM protein. SCA is a genetically engineered fused single chain molecule containing the variable region of the light chain and the variable region of the heavy chain linked by a suitable polypeptide linker. Methods for making these fragments are known in the art, see e.g., Harlow and Lane, *Antibodies: A Laboratory Manual*, Cold Spring Harbor Laboratory, New York (1988).

As discussed previously, minor modifications of the OM proteins' primary amino acid sequences may result in proteins which have substantially equivalent function compared to the OM proteins described herein. Such modifications may be deliberate, as by site-directed mutagenesis, or may be spontaneous. All proteins produced by these modifications are included herein as long as OM protein functions exist.

Isolation and purification of microbially expressed proteins, or fragments thereof, provided by the invention, may be carried out by conventional means including preparative chromatography and immunological separations involving monoclonal or polyclonal antibodies.

The invention extends to any host modified proteins according to the methods described, or modified by any other methods, commonly known to those of ordinary skill in the art, such as, for example, by transfer of genetic material using a lysogenic phage, and which result in a prokaryote expressing the leptospiral gene for an OM protein. Prokaryotes transformed with the leptospiral gene encoding an OM protein are particularly useful for the production of proteins which can be used for the immunization of an animal.

In one embodiment, the invention provides a pharmaceutical composition useful for inducing an immune response to pathogenic Leptospira species in an animal comprising an immunologically effective amount of one or more OM proteins in a pharmaceutically acceptable carrier. The term "immunogenically effective amount," as used in describing the invention, is meant to denote that amount of leptospiral antigen which is necessary to induce in an animal the production of an immune response to Leptospira species. The OM proteins are particularly useful in sensitizing the immune system of an animal such that, as one result, an immune response is produced which ameliorates the effect of Leptospira species infection.

OM proteins i.e., their variants, functional equivalents, and derivatives, which are effective vaccines against leptospirosis, can be screened for using the methods described in Bolin, C. A., et al., *Am. J. Vet. Res.*, 52:1639–1643 (1991) and Bey, R. F., et al., *Infect. Immun.*, 10:1051–1056 (1974). The vaccination methods disclosed in these references can also be used for vaccinating animals with one or more OM proteins.

OM proteins can be administered, alone or in combination, e.g. parenterally by injection, rapid infusion, nasopharyngeal absorption, dermal absorption, and enterally, e.g., orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water.

Besides the inert diluents, such compositions can also include adjuvants, wetting agents, emulsifying and suspending agents, and sweetening, flavoring, and perfuming agents.

For example, recombinant bacteria and viruses expressing one or more OM proteins can be used as vaccines in the above compositions, and be administered, e.g. orally. The vaccines can also be added to baits against potential carriers of Leptospira species such as rodents so that they will not be infected by Leptospira species and be carriers in spreading Leptospira species and the disease to humans and other animals, such as domestic animals.

It is also possible for the antigenic preparations containing one or more OM proteins of the invention to include an adjuvant. Adjuvants are substances that can be used to nonspecifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete Adjuvants), mineral salts {for example, AlK(SO$_4$)$_2$, AlNa (SO$_4$)$_2$, AlNH$_4$(SO$_4$), silica, alum, Al(OH)$_3$, Ca$_3$(PO$_4$)$_2$, kaolin, and carbon}, polynucleotides (for example, poly IC and poly AU acids), and certain natural substances (for example, wax D from *Mycobacterium tuberculosis*, as well as substances found in *Corynebacterium parvum, Bordetella pertussis*, and members of the genus Brucella).

In another embodiment, a method of inducing an immune response to pathogenic Leptospira species in animal is provided. Many different techniques exist for the timing of the immunizations when a multiple immunization regimen is utilized. It is possible to use the antigenic preparation of the invention more than once to increase the levels and diversity of expression of the immune response of the immunized animal. Typically, if multiple immunizations are given, they will be spaced two to four weeks apart. Subjects in which an immune response to Leptospira species is desirable include any animal susceptible to Leptospira species infection. The animals are preferably mammals. Examples of the mammals are: humans, domestic and wild mammals. The domestic mammals include: livestock such as cattle, swine, goats, horses, buffaloes; and pets such as dogs.

Generally, the dosage of one or more of the OM proteins administered to an animal will vary depending on such factors as age, condition, sex and extent of disease, if any, and other variables which can be adjusted by one of ordinary skill in the art.

The antigenic preparations of the invention can be administered as either single or multiple dosages and can vary, e.g. from about 10 μg to about 1,000 μg for the leptospiral OM antigen per dose, more preferably from about 50 μg to about 700 μg OM antigen per dose, most preferably from about 50 μg to about 300 μg OM antigen per dose.

When used for immunotherapy, the antibodies, preferably monoclonal antibodies or SCA, of the invention may be unlabeled or labeled with a therapeutic agent. These agents can be coupled either directly or indirectly to the antibodies of the invention. One example of indirect coupling is by use of a spacer moiety. These spacer moieties, in turn, can be either insoluble or soluble {Diener, et al., *Science*, 231:148 (1986)} and can be selected to enable drug release from the antibody molecule at the target site. Examples of therapeutic agents which can be coupled to the antibodies for immunotherapy are drugs, radioisotopes, lectins, and toxins.

The labeled or unlabeled antibodies can also be used in combination with therapeutic agents such as those described above. Especially preferred are therapeutic combinations comprising the antibody and immunomodulators and other biological response modifiers.

When the antibody is used in combination with various therapeutic agents, such as those described herein, the administration of the antibody and the therapeutic agent usually occurs substantially contemporaneously. The term "substantially contemporaneously" means that the antibody and the therapeutic agent are administered reasonably close together with respect to time. Usually, it is preferred to administer the therapeutic agent before the antibody. For example, the therapeutic agent can be administered 1 to 6 days before the antibody. The administration of the therapeutic agent can be daily, or at any other interval, depending upon such factors, for example, as the nature of the disorder, the condition of the patient and half-life of the agent.

The dosage ranges for the administration of antibodies are those large enough to produce the desired effect in which the onset symptoms of the leptospiral disease are ameliorated. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician in the event of any complication. Dosage can vary, e.g., from about 0.1 mg/kg to about 2000 mg/kg, preferably about 0.1 mg/kg to about 500 mg/kg, in one or more dose administrations daily, for one or several days. Generally, when the antibodies are administered conjugated with therapeutic agents, lower dosages, comparable to those used for in vivo diagnostic imaging, can be used.

The antibodies can be administered parenterally by injection or by gradual perfusion over time. The antibodies can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases, preferably isolated or substantially pure, and the like.

An animal may also be vaccinated or treated using the disclosed, preferably isolated or in substantially pure composition, nucleic acid sequences, their mutagenized sequences or fragments thereof, which may be directly administered or incorporated into a plasmid and administered into the animal. The nucleic acid sequences may be mixed with a pharmaceutically acceptable carrier prior to administration. The administrations may be by means of microinjection or particle bombardment using methods known in the art. For example, the injection may be by means of a gene gun, such as described in Yang, N.-S. et al., *Gene Therapy via Particle Bombardment: Applications of the Accell Gene Gun*, in *Gene Therapeutics: Methods and Applications of Direct Gene Transfer*, Wolff, J. A., ed., Birkhauser, USA (1994).

In a further embodiment, the invention provides a method of detecting a pathogenic Leptospira species-associated disorder in a subject comprising contacting a cell component with a reagent which binds to the cell component. The cell component can be nucleic acid, such as DNA or RNA, or it can be protein. When the component is nucleic acid, the reagent is a nucleic acid probe or polymerase chain reaction ("PCR") primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for an OM protein may be used to detect the presence of the respective OM protein (using antibody) or polynucleotide (using nucleic acid probe) in biological samples. Any specimen containing a detectable amount of the OM antigen or polynucleotide can be used. Preferred specimens of this invention are a biological fluid or tissue sample. Preferred examples of a biological fluid sample include: blood, serum, plasma, tear, milk, urine, and cerebrospinal fluid. Preferred examples of a biological tissue sample include tissue samples from the liver and kidney and tissue of endothelial origin.

When the cell component is nucleic acid, it may be necessary to amplify the nucleic acid prior to binding with a Leptospira species specific probe. Preferably, PCR is used, however, other nucleic acid amplification procedures such as ligase chain reaction ("LCR"), ligated activated transcription ("LAT") and nucleic acid sequence-based amplification ("NASBA") may be used.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, an OM protein can be used to detect antibodies to the respective OM protein in a specimen. The OM proteins of the invention is particularly suited for use in immunoassays in which they can be utilized in liquid phase or bound to a solid phase carrier. In addition, the OM proteins used in these assays can be detectably labeled in various ways.

Examples of immunoassays which can utilize the OM proteins are competitive and noncompetitive immunoassays in either a direct or indirect format. Examples of such immunoassays are the radioimmunoassay ("RIA"), the sandwich (immunometric assay) and the Western blot assay. Detection of antibodies which bind to one or more of the OM proteins of the invention can be done utilizing immunoassays which run in either the forward, reverse, or simultaneous modes, including immunohistochemical assays on biological samples. The concentration of an OM protein which is used will vary depending on the type of immunoassay and nature of the detectable label which is used. However, regardless of the type of immunoassay which is used, the concentration of the OM proteins utilized can be readily determined by one of ordinary skill in the art using routine experimentation.

The OM proteins of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding a particular OM protein or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the antibody which binds to an OM protein may be present in various biological samples. Any sample containing a detectable amount of antibodies to an OM protein can be used. Preferred specimens of this invention are: a biological fluid or tissue sample. Preferred examples of a biological fluid sample include: blood, serum, plasma, tear, milk, urine, and cerebrospinal fluid. Preferred examples of a biological tissue sample include tissue samples from the liver and kidney and tissue of endothelial origin.

The antibodies of the invention, preferably monoclonal antibodies and SCA, directed toward an OM protein, are also useful for the in vivo detection of antigen. The detectably labeled antibody is given in a dose which is diagnostically effective. The term "diagnostically effective" means that the amount of detectably labeled monoclonal antibody is administered in sufficient quantity to enable detection of leptospiral OM antigen for which the antibodies are specific.

The concentration of detectably labeled antibody which is administered should be sufficient such that the binding to those cells, body fluid, or tissue having one or more of the OM proteins is detectable compared to the background. Further, it is desirable that the detectably labeled antibody be rapidly cleared from the circulatory system in order to give the best target-to-background signal ratio.

As a rule, the dosage of detectably labeled antibody for in vivo diagnosis will vary depending on such factors as age, sex, and extent of disease of the subject. The dosage of antibody can vary, e.g., from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid ("DTPA") and ethylenediaminetetraacetic acid ("EDTA") and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The antibodies of the invention can also be labeled with a paramagnetic isotope for purposes of in vivo diagnosis, as in magnetic resonance imaging ("MRI") or electron spin resonance ("ESR"). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The antibodies, preferably monoclonal antibodies and SCA, of the invention can also be used to monitor the course of amelioration of Leptospira species associated disorder. Thus, by measuring the increase or decrease of one or more of the leptospiral OM proteins or antibodies to one or more of the OM proteins present in various body fluids or tissues, it would be possible to determine whether a particular therapeutic regiment aimed at ameliorating the disorder is effective.

The materials for use in the method of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a binding reagent which binds one or more of the OM proteins, such as an antibody. A second container may further comprise one or more of the OM proteins. The constituents may be present in liquid or lyophilized form, as desired.

In the above discussion, the diagnostic tests, e.g. nucleic acid hybridization assays or immunoassays, may test for one or more of the OM proteins. Alternatively, they may consist of panel tests which test for both the OM proteins or OM nucleotide sequences, in combination with other proteins or nucleic acid sequences specific for Leptospira species, in particular pathogenic Leptospira species, such as OmpL1 {Haake, D. A., et al., *J. Bacteriol.*, 175:4225–4234 (1993); U.S. patent application Ser. No. 08/040,747, "Cloned Leptospira Outer Membrane Protein" to Haake, D. A., et al., filed on Mar. 31, 1993} and OmpL2 {U.S. patent application Ser. No. 08/249,013, "Cloned Leptospira Outer Membrane Protein" to Haake, D. A., et al., filed on May 25, 1994}. Similarly, the compositions, e.g. for immunoassays or vaccinations, may consist of an OM protein, singly. Alternatively, they may consist of a cocktail containing more than one OM protein, or these proteins in combination with other proteins specific for Leptospira species, in particular pathogenic Leptospira species, such as OmpL1 and OmpL2. The antibody compositions may consist of antibodies specific to an OM protein. Alternatively, they may consist of a cocktail containing antibodies to more than one OM protein, or to these proteins and other proteins specific for Leptospira species, in particular pathogenic Leptospira species, such as OmpL1 and OmpL2. The hybridization assays are preferably run at moderate to stringent conditions. The immunoassays are preferably conducted under conditions of reduced non-specific binding. Thus, the test kits and methods using these compositions are varied accordingly.

The following examples are intended to illustrate but not limit the invention. While they are typical of those that might be used, other procedures known to those skilled in the art may alternatively be used.

EXAMPLES

Example 1

ISOLATION OF LEPTOSPIRA PROTEINS USING THE FIRST TWO METHODS

The following example describes the isolation of twelve OM proteins having the molecular weights of approximately 22-, 24-, 37-, 46-, 51-, 56-, 67-, 70-, 74-, 93-, 101-, and 127-kDa, respectively.

Materials and Methods

Bacterial strains, media, and plasmids. *Leptospira kirschneri*, strain RM52 {formerly *L. alstoni*, Thierman, et al., *Ann. Proc. Amer. Assn. Veterinary Laboratory Diagnosticians*, 27:233–244 (1984); Haake, et al., *J. Bacteriol*, 175:4225–4234 (1993)}, and other Leptospira species were received from C. A. Bolin (National Animal Disease Center, Agricultural Research Service, U.S. Department of Agriculture, Ames, Iowa) and passaged in bovine serum albumin Tween-80 medium (bovuminar PLM-5 microbiological media, Intergen).

Antisera. Antisera to LipL36 and LipL41 was prepared as previously described for OmpL1 {Haake, et al., *J. Bacteriol.*, 175:4225 (1993)}. Briefly, New Zealand White rabbits were immunized with purified $His_6$ fusion proteins, expressed by *E. coli* JM109 (Invitrogen) transformed with the pRSET plasmid (Invitrogen) containing the genes encoding the respective proteins. Rabbit antiserum to the 32-kDa MOMP and anti-flagellar monoclonal antibody 1H8 were generous gifts of Dr. Richard Zuerner, National Animal Disease Center, USDA, Ames, Iowa. Rabbit antiserum to leptospiral GroEL was a generous gift of Dr. Ben Adler, Department of Microbiology, Monash University, Australia.

Gel electrophoresis and immunoblotting. Samples for SDS-PAGE were solubilized in final sample buffer ("FSB") composed of 62.5 mM Tris hydrochloride (pH 6.8), 10% glycerol, 5% 2-mercaptoethanol, and 2% SDS. Samples for immunoblots to be probed with OmpL1 antiserum were solubilized in FSB containing 8M urea. Proteins were separated on a 12% gel with a discontinuous buffer system {Laemmli, *Nature* (London), 227:680–685 (1970)} and stained with Coomassie brilliant blue, silver {Wray, et al., *Anal. Biochem.*, 118:197–203 (1981)}, or periodate silver {Tsai, et al., *Anal. Biochem.*, 119:115–119 (1982)} or were transferred to nitrocellulose (Schleicher & Schuell Inc, Keene, N.H.) for immunoblotting. For antigenic detection on immunoblots, the nitrocellulose was blocked with 5% nonfat dry milk in PBS—0.1% Tween-20 ("PBS-T"), incubated for one hour with antiserum diluted 1:5000 (unless otherwise noted) in PBS-T, and proved with Donkey anti-rabbit antiserum conjugated to horseradish peroxidase (Amersham Corporation, Arlington Heights, Ill.). Antigen-antibody binding was detected using the Enhanced Chemiluminescence System ("ECL", Amersham). Blots were incubated in ECL reagents for one minute and then exposed to XAR-5 film (Kodak).

*L. kirschneri* OM isolation in citrate/NaCl. *L. kirschneri* ($8\times10^{10}$) were washed once in phosphate buffered saline (pH 7.4). The pellet was resuspended in 70 ml of 25 mM citrate pH 3.2, 1 M NaCl. The leptospiral suspension was placed in a sterile 100 ml flask with a magnetic stir bar and mixed for two hours at room temperature. The suspension was centrifuged at 28,000 rpm (SW28 rotor) for one hour to pellet membranes. The pellet was thoroughly resuspended in 25 mM citrate pH 3.2, 1M NaCl containing 27% sucrose (w/v) and loaded on a continuous 27–55% sucrose (w/v) gradient (in 25 mM citrate pH 3.2, 1M NaCl) in Beckman ultraclear tubes and centrifuged overnight at 40,000 rpm in an SW41 rotor. The entire gradient was separated into 0.4 ml fractions by pipetting from the top of the gradient. The refractive index of each fraction was measured with a refractometer. Due to a contaminant in the citric acid, trichloroacetic acid ("TCA") precipitation had to be performed prior to determining the protein concentration on the fractions using the BCA protein assay system (Pierce BCA Applications Note #12, Pierce Chemicals Co., Rockford, Ill.). β-NADH oxidase activity was measured as described below. Material for SDS-PAGE and/or immunoblot analysis was obtained by TCA precipitation performed by incubation with 4 volumes of 5% TCA for sixteen hours at 4° C. Precipitated material was collected by centrifugation for fifteen minutes at top speed in a microfuge, washed with acetone, centrifuged for five minutes at top speed in a microfuge, then resuspended in sample buffer.

*L. kirschneri* OM isolation in sucrose/NaCl. *L. kirschneri* ($4\times10^{10}$) were washed once in phosphate buffered saline (pH 7.4). The pellet was resuspended in 4 ml of TNSEDR buffer consisting of 10 mM Tris pH 9, 1M NaCl, 27% sucrose (w/v), 2 mM EDTA, 1 unit/ml DNAse, and 0.25 microgram/ml RNAse. The leptospiral suspension was placed in a 2059 tube (Falcon) with a magnetic stir bar. After mixing for four hours at room temperature the suspension was centrifuged for fifteen minutes at 3000×g to remove aggregated material. The supernatant was loaded on a continuous 27–55% sucrose (w/v) gradient (in 10 mM Tris pH 9, 1M NaCl, 2 mM EDTA) in Beckman ultraclear tubes and centrifuged overnight at 28,000 rpm in an SW28 rotor. The entire gradient was separated into 0.8 ml fractions by pipetting from the top of the gradient. The refractive index of each fraction was measured with a refractometer. The protein concentration was determined on the fractions using BCA protein assay system of Pierce Chemicals Co. (Rockford, Ill.). β-NADH oxidase activity was measured as described below. Material for SDS-PAGE and/or immunoblot analysis was obtained by TCA precipitation as described above.

β-NADH oxidase assay. β-NADH oxidase assays were conducted as described previously {Osborn, et al., *J. Biol. Chem.*, 247:3962–3972 (1972); Norris, et al., *Microbiol. Rev.*, 57:750–779 (1993); Skare, et al., *J. Clin. Invest.*, 96:2380–2392 (1995); Stanton, et al., *J. Bacteriol.*, 175:2980–2987 (1993)} except that 0.5 mM DTT was added to all buffers used in the outer membrane isolation procedure. A sample of each fraction was diluted in 50 mM Tris pH 7.5, 0.2 mM DTT, and 0.1 mM β-NADH and incubated in the dark at room temperature. The amount of β-NADH present in each sample was determined by measuring the absorbance at 340 nm at the beginning and end of the incubation period. The amount of β-NADH oxidase activity was determined by the rate of β-NADH catalysis.

RESULTS

*L. kirschneri* OM isolation in citrate/NaCl. When the hypotonic citrate technique developed for OM isolation from Treponema species and *B. burgdorferi* was applied without modification, there was insufficient recovery of the leptospiral OM. Modifications of the hypotonic citrate technique included addition of 1M NaCl during all stages of isolation procedure. In addition, it was essential to thoroughly resuspend the ultracentrifugation pellet in 25 mM citrate pH 3.2, 1M NaCl containing 27% sucrose (w/v) prior to loading on the sucrose gradient.

After ultracentrifugation of the sucrose gradient, three discrete bands were visible, two light bands (L1c and L2c) and one heavy band (Hc). Results of refractive index analysis were as follows:

| Band | Fraction # | Refractive Index | Density (g/ml) | Sucrose Density (w/w) |
|------|-----------|------------------|----------------|----------------------|
| L1c  | 17        | 1.398            | 1.17           | 39.2%                |
| L2c  | 19        | 1.401            | 1.18           | 40.7%                |
| Hc   | 28        | 1.416            | 1.22           | 48.0%                |

Figures 1, 2:
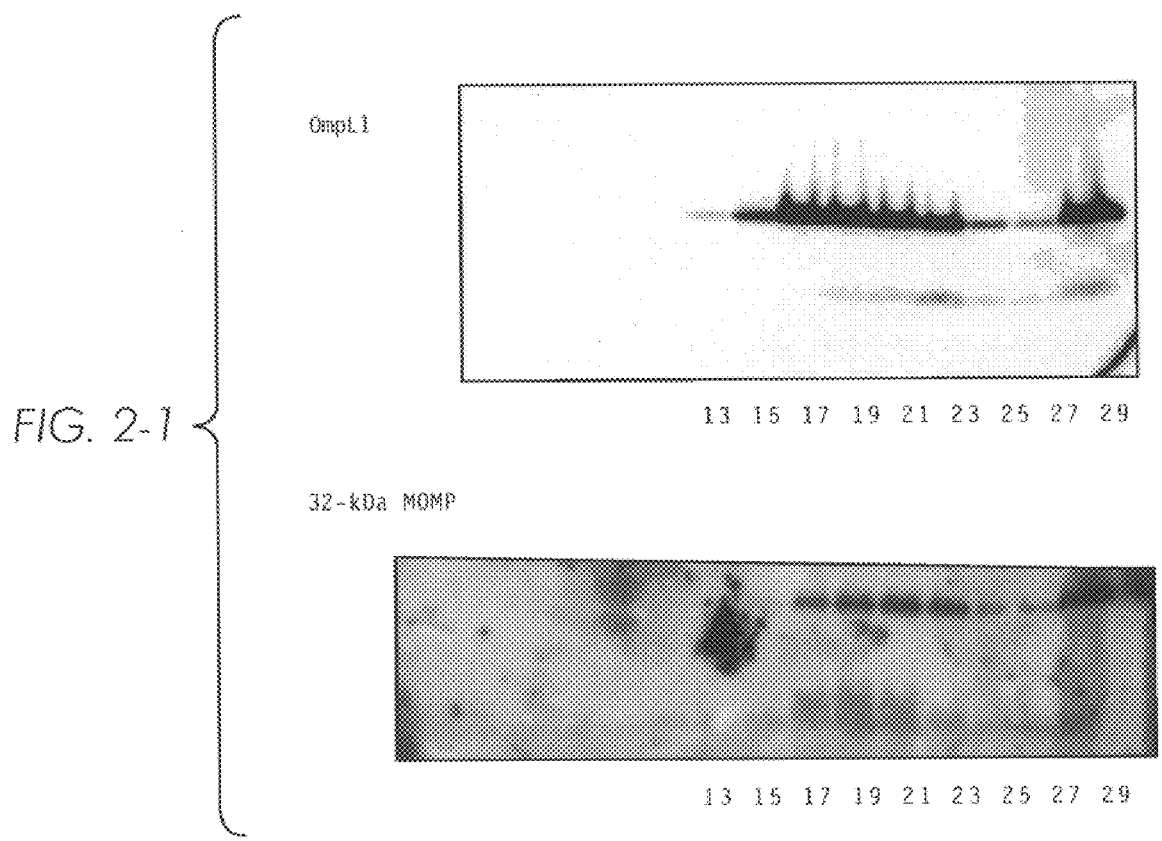
FIG. 2 presents immunoblots of trichloroacetic acid ("TCA") precipitated fractions from sucrose gradient of *L. kirschneri* treated with Citrate/NaCl. Samples were probed with antisera specific for OmpL1, 32-kDa major outer membrane protein ("MOMP"), LipL36, LipL41, flagella, and GroEL.
Figure 2:
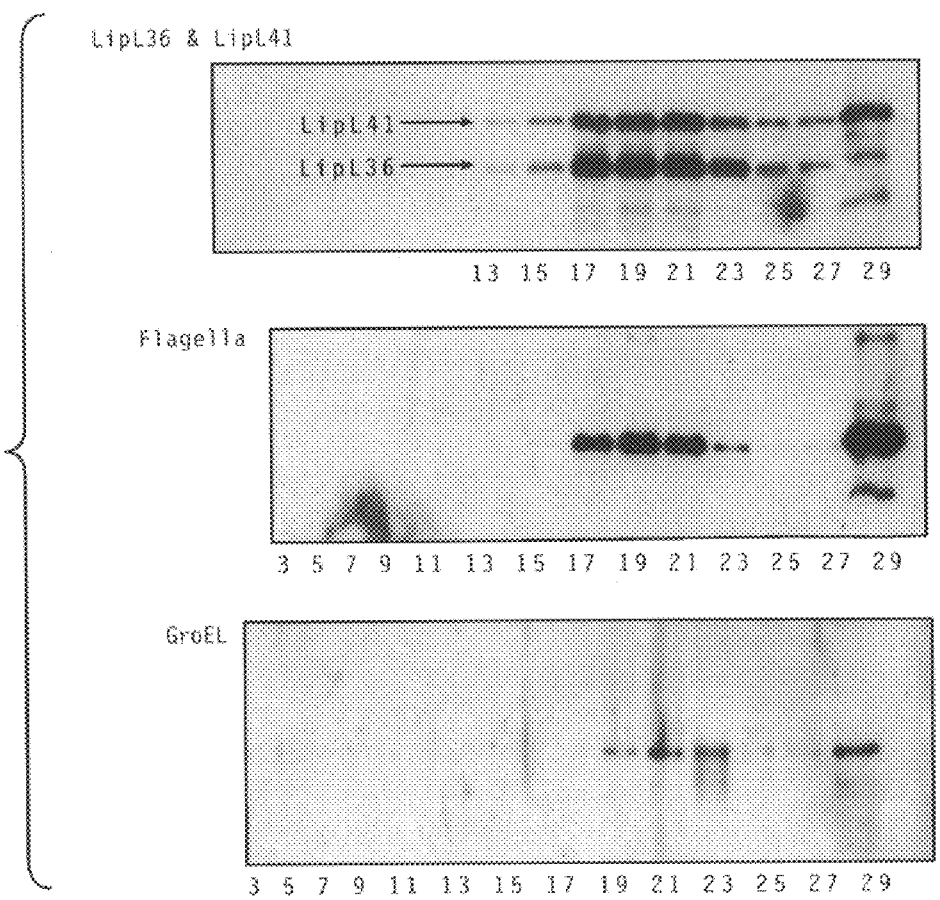
Figure 3:
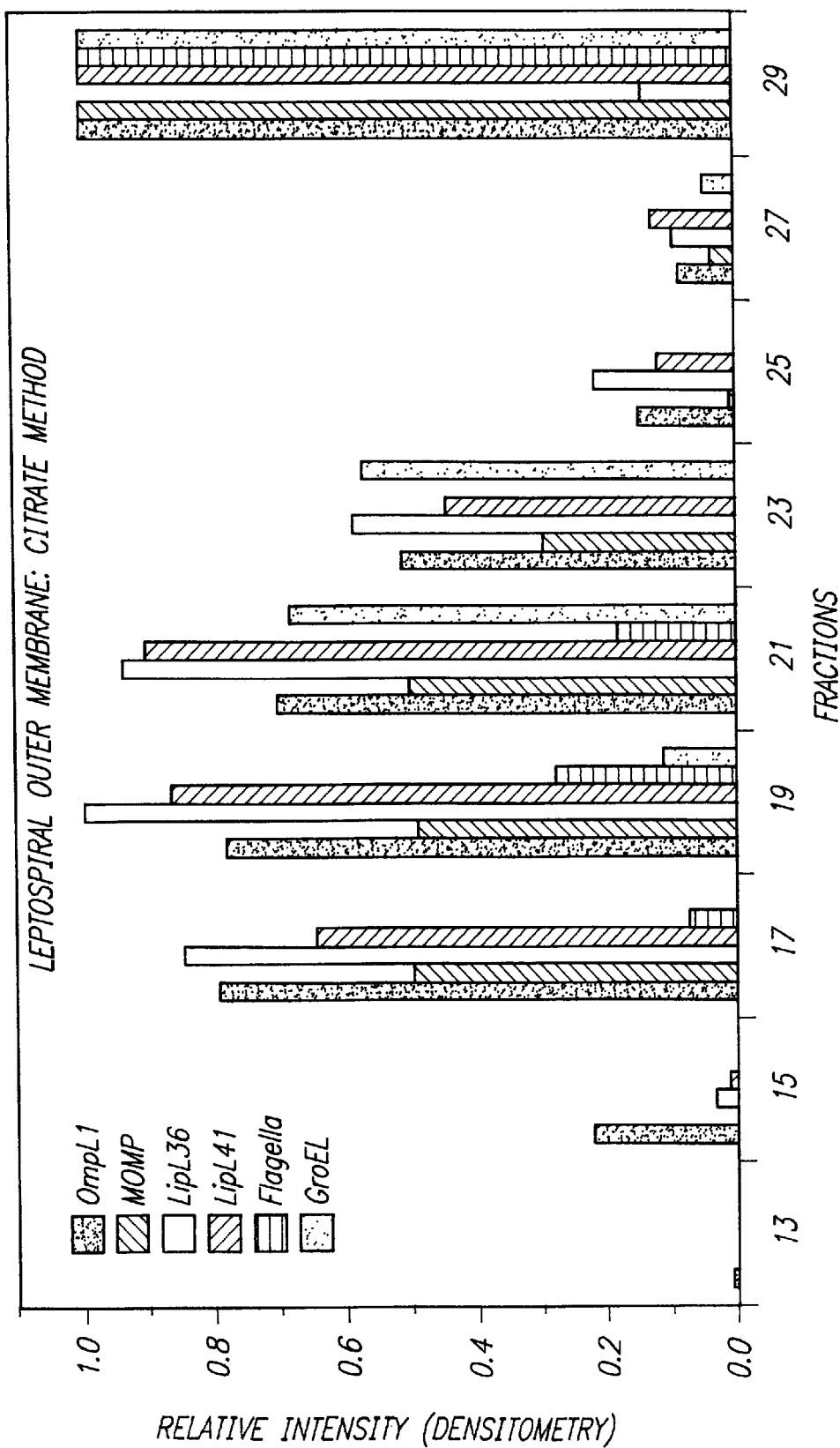
FIG. 3 presents results of densitometric analysis of immunoblots of TCA precipitated fractions from sucrose gradient of *L. kirschneri* treated with Citrate/NaCl.
Figure 4:
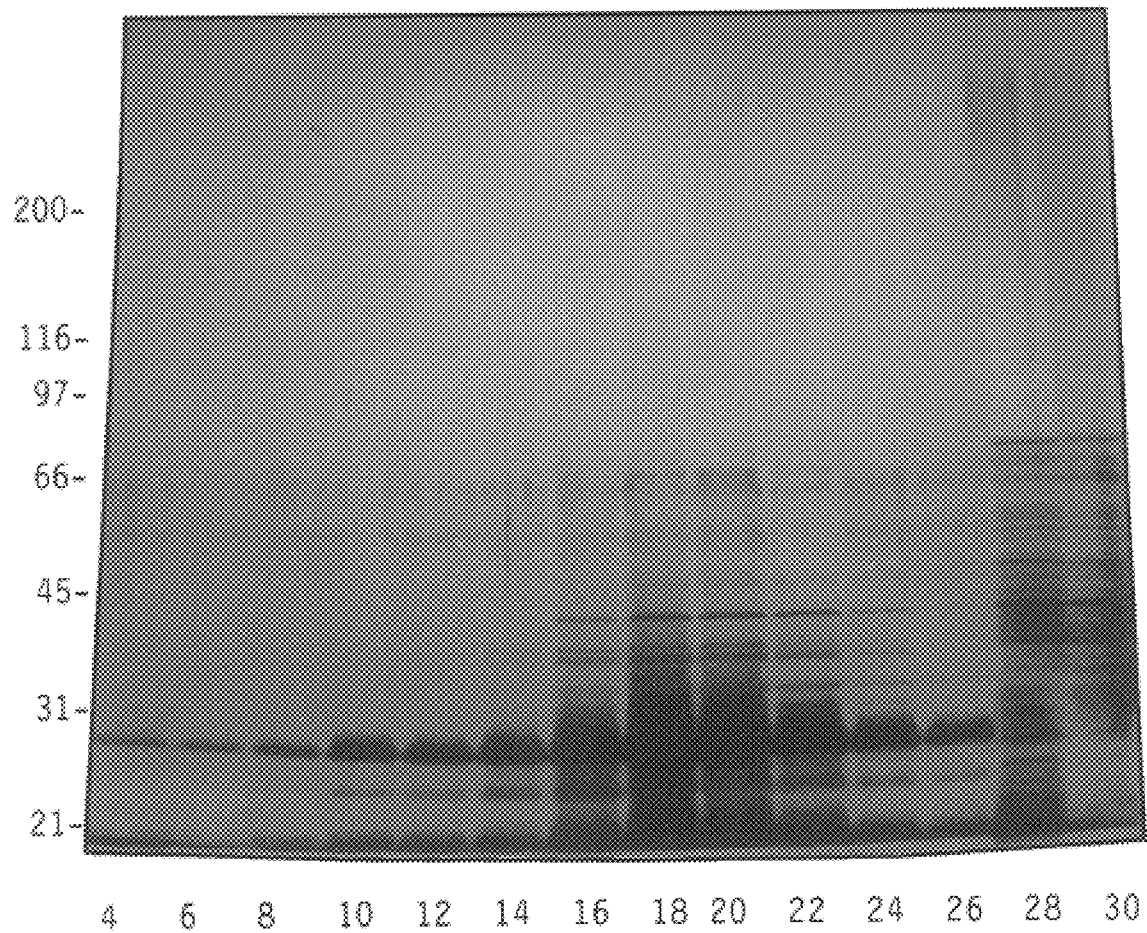
FIG. 4 presents protein silver stain of fractions from sucrose gradient of *L. kirschneri* treated with Citrate/NaCl.

The protein concentration of the fractions gradually increased as the sucrose density increased, peaking in fraction #28, which contained band Hc and the majority of PC material (FIG. 1). The fraction containing band Hc contained $4.7 \times 10^{-4}$ IU of β-NADH oxidase activity. No β-NADH oxidase activity was found in any of the other fractions. Immunoblot analysis revealed that band Hc also contained most of the leptospiral GroEL and flagella (FIG. 2). Although some GroEL and flagella was found in band L2c, band L1c contained no GroEL and only a small amount of flagella. As determined by densitometric analysis (FIG. 3), band L1c contained in fraction 17 contained less than 10% of the amount of flagella found in band Hc. This result suggests that the more buoyant material in band L1c was more free of PC contaminants than band L2c. Bands L1c and L2c contained >50% of the amounts of porin OmpL1, lipoproteins LipL36 and LipL41, and the 32-kDa MOMP relative to the amounts found in band Hc. Release of these proteins from the PC material in band Hc was best for LipL36, as determined by densitometric analysis (FIG. 3). Analysis of the citrate/NaCl fractions by periodate silver stain revealed that the amount of leptospiral LPS peaked in fractions 17–21, which contained bands L1c and L2c (data not show). Protein silver stain of the citrate gradient fractions revealed that in addition to the 32-kDa MOMP, LipL36, and LipL41, several additional bands were enriched in bands L1c and L2c, including proteins with molecular masses of approximately 37-, 46-, 67-, 70-, 74-, and 101-kDa (FIG. 4).

*L. kirschneri* OM isolation in sucrose/NaCl. The hypertonic sucrose technique developed for OM isolation from Treponema species and *B. burgdofferi* was applied without modification, there was poor recovery of the leptospiral OM. Addition of 1M NaCl greatly improved release of OmpL1 and leptospiral LPS from the PC fraction. In addition, simple rocking of the bacterial suspension in the sucrose/NaCl solution was insufficient to release the leptospiral OM. Stirring with a magnetic microstirbar (2 mm diameter) provided the proper amount of mechanical agitation for OM release. The size of the stirbar and the rate of mixing were important. It was found that contamination of the OM fraction with PC components could occur if the bacterial suspension was mixed too rapidly with a larger diameter stirbar (5/16").

After ultracentrifugation of the sucrose gradient, three discrete bands were visible, two light bands (L1s and L2s) and one heavy band (Hs). Results of refractive index analysis were as follows:

| Band | Fraction # | Refractive Index | Densiy (g/ml) | Sucrose Density (w/w) |
|------|-----------|------------------|---------------|----------------------|
| L1s  | 14        | 1.393            | 1.16          | 36.4%                |
| L2s  | 22        | 1.402            | 1.18          | 41.1%                |
| Hs   | 34        | 1.416            | 1.22          | 48.0%                |

Figure 5:
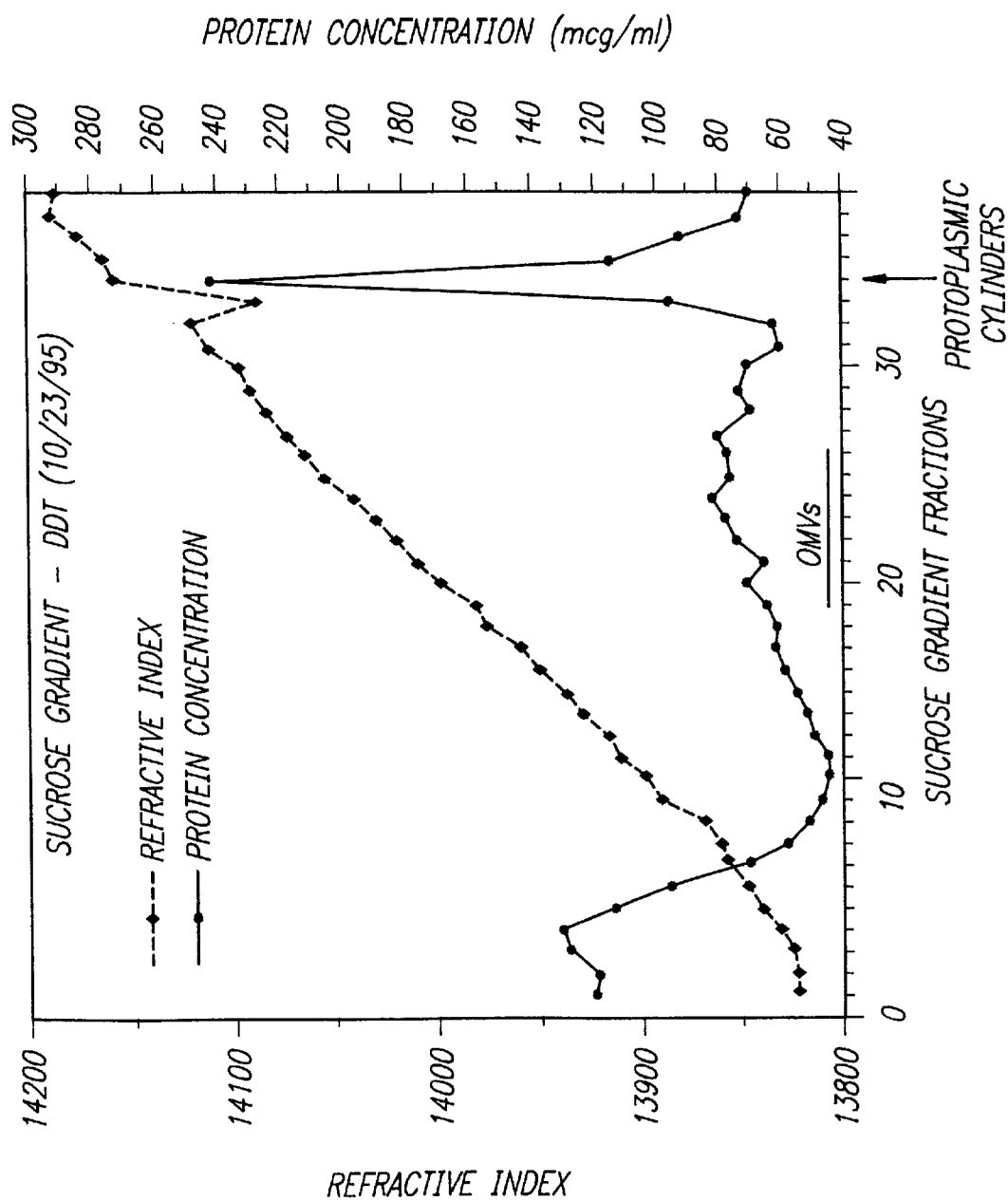
FIG. 5 presents sucrose gradient fractionation of *L. kirschneri* treated with Sucrose/NaCl. Fractions were tested for refractive index and protein concentration.
Figures 1, 6:
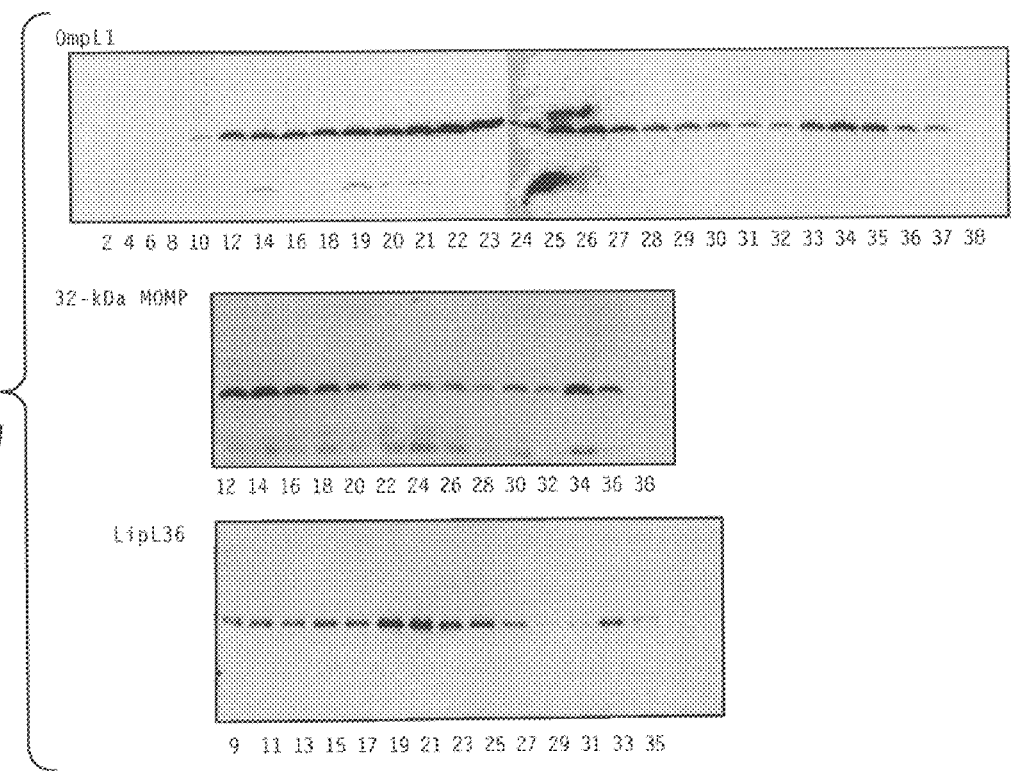
FIG. 6 presents immunoblots of TCA precipitated fractions from sucrose gradient of *L. kirschneri* treated with Sucrose/NaCl. Samples were probed with antisera specific for OmpL1, 32-kDa MOMP, LipL36, LipL41, flagella, and GroEL.
Figures 2, 6:
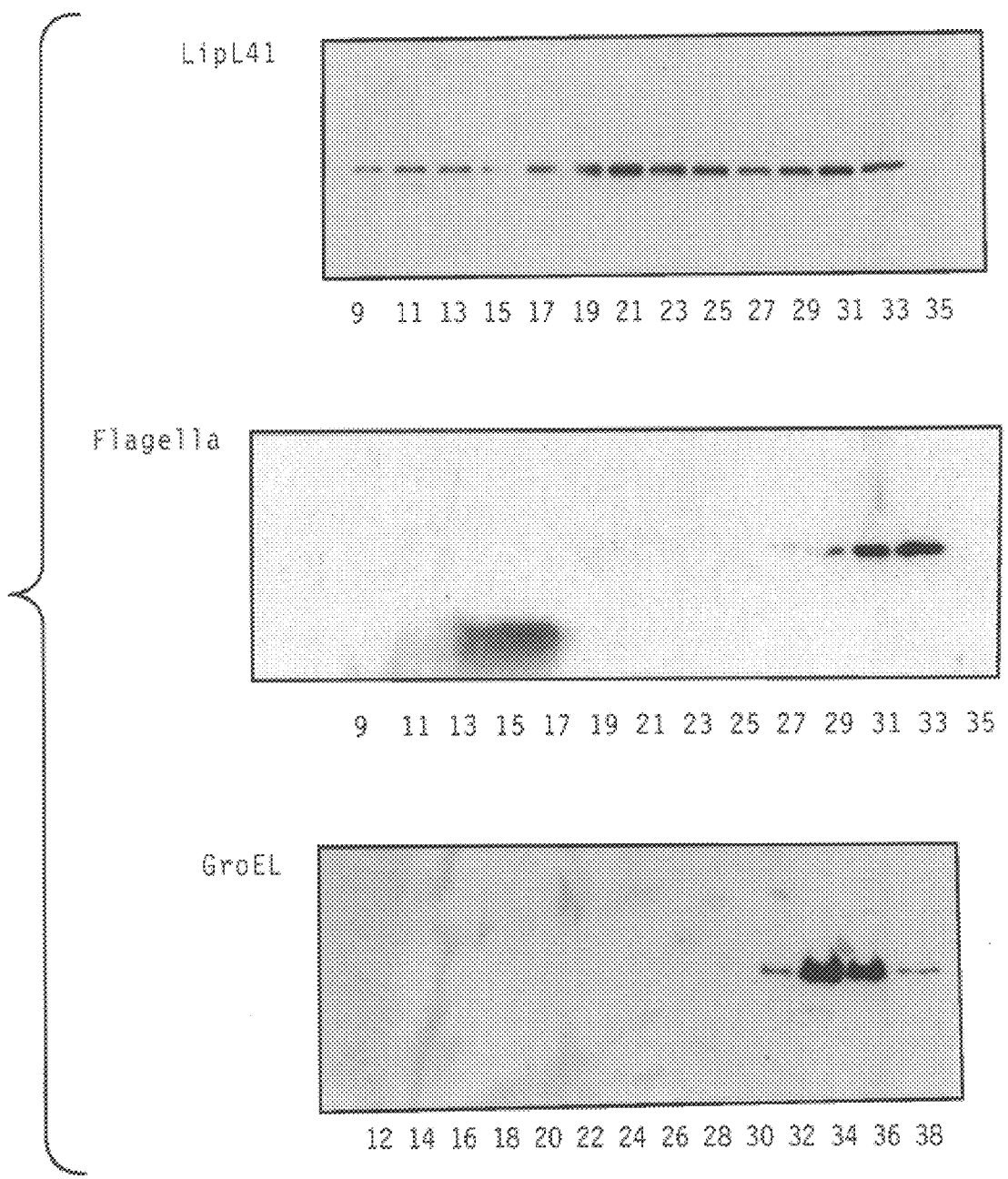
Figure 7:
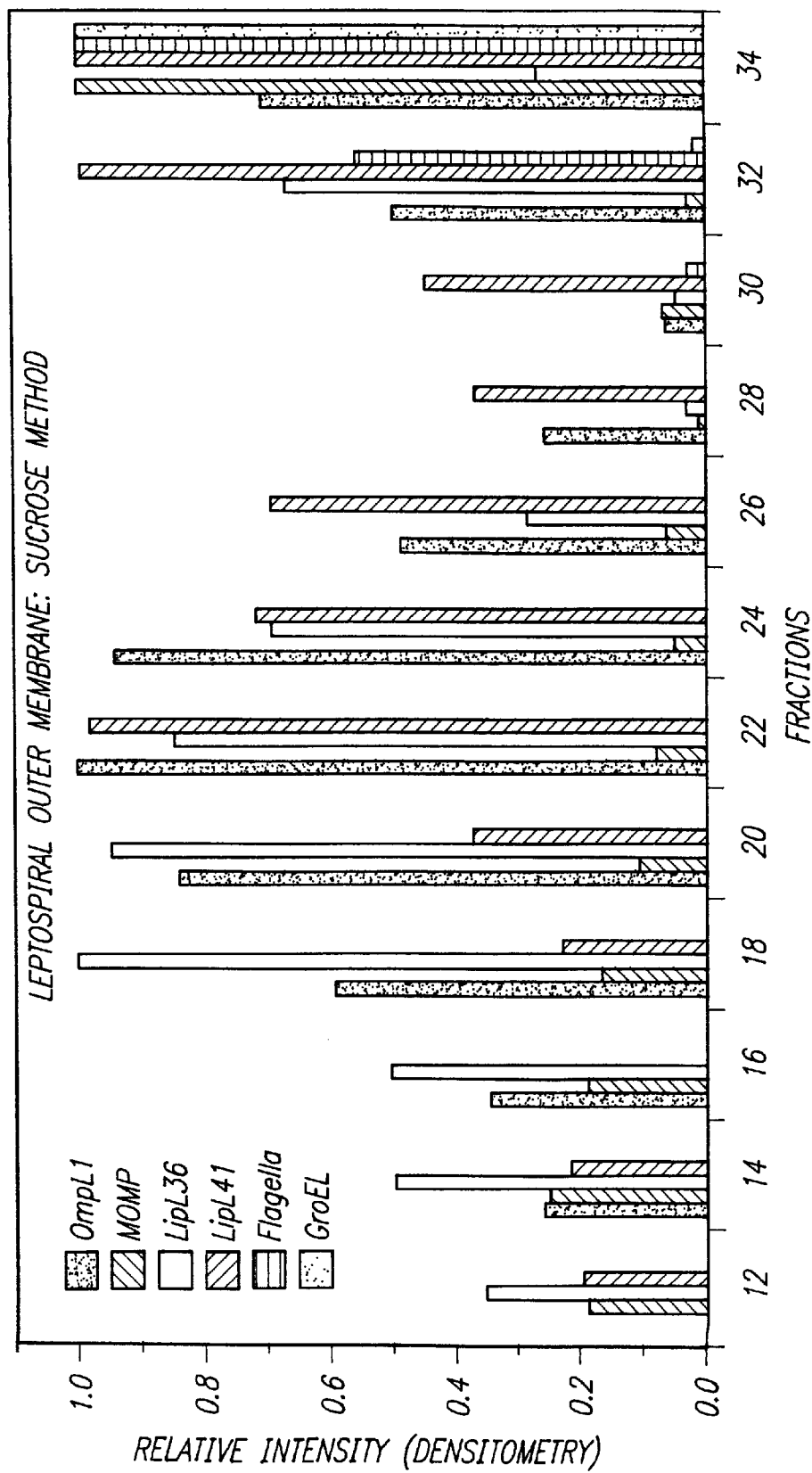
FIG. 7 presents results of densitometric analysis of immunoblots of TCA precipitated fractions from sucrose gradient of *L. kirschneri* treated with Sucrose/NaCl.
Figure 8:
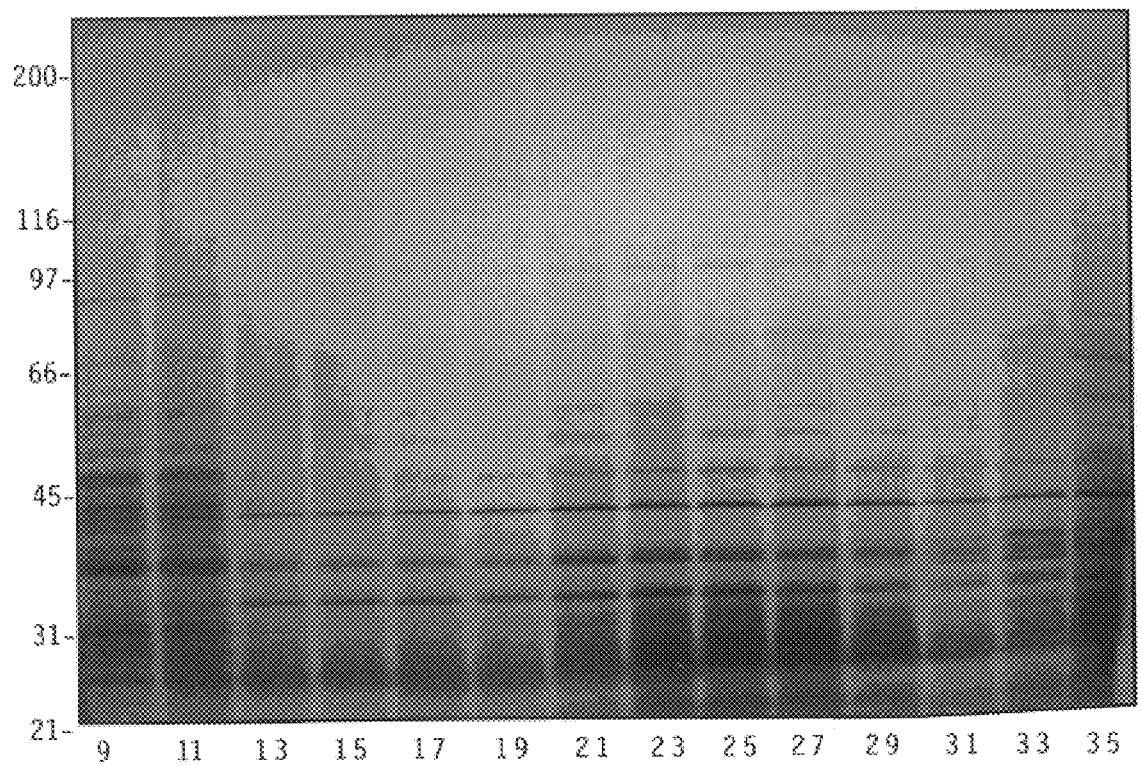
FIG. 8 presents protein silver stain of fractions from sucrose gradient of *L. kirschneri* treated with Sucrose/NaCl.

The protein concentration of the sucrose gradient fractions peaked in three places (FIG. 5.). The first protein peak occurred in the most buoyant portion of the gradient containing leptospiral proteins that were unable to enter the gradient. The second protein peak contained band L2s and the highest concentration of OM components OmpL1 and leptospiral LPS, as determined by immunoblot (FIG. 6) and periodate silver stain (data not shown). The third protein peak contained band Hc and the majority of PC material. Fraction #34 containing band Hs contained the most β-NADH oxidase activity: $8.8 \times 10^{-4}$ IU. Although some β-NADH oxidase activity was found in fractions denser than fraction #34, no β-NADH oxidase activity was found in any of the more buoyant fractions. Immunoblot analysis revealed that band Hs also contained most of the leptospiral GroEL and flagella (FIG. 6). No GroEL or flagella was found in bands L1s or L2s. Band L1s contained the highest concentration of the 32-kDa MOMP while band L2s contained the highest concentration of the porin OmpL1, and the lipoproteins LipL36 and LipL41. Release of these proteins from the PC material in band Hc was best for LipL36, as determined by densitometric analysis (FIG. 7). Protein silver stain of the citrate gradient fractions that in addition to the 32-kDa MOMP, LipL36, and LipL41, several additional bands were enriched in bands L2s, including proteins with molecular masses of approximately 22-, 24-, 46-, 51-, 56-, 67-, 70-, 74-, 93-, 101-, and 127-kDa (FIG. 8).

Example 2

ISOLATION OF LEPTOSPIRA PROTEINS USING FRENCH PRESS AND DIGOXIGENIN-AMPICILLIN CONJUGATES

Figure 9:
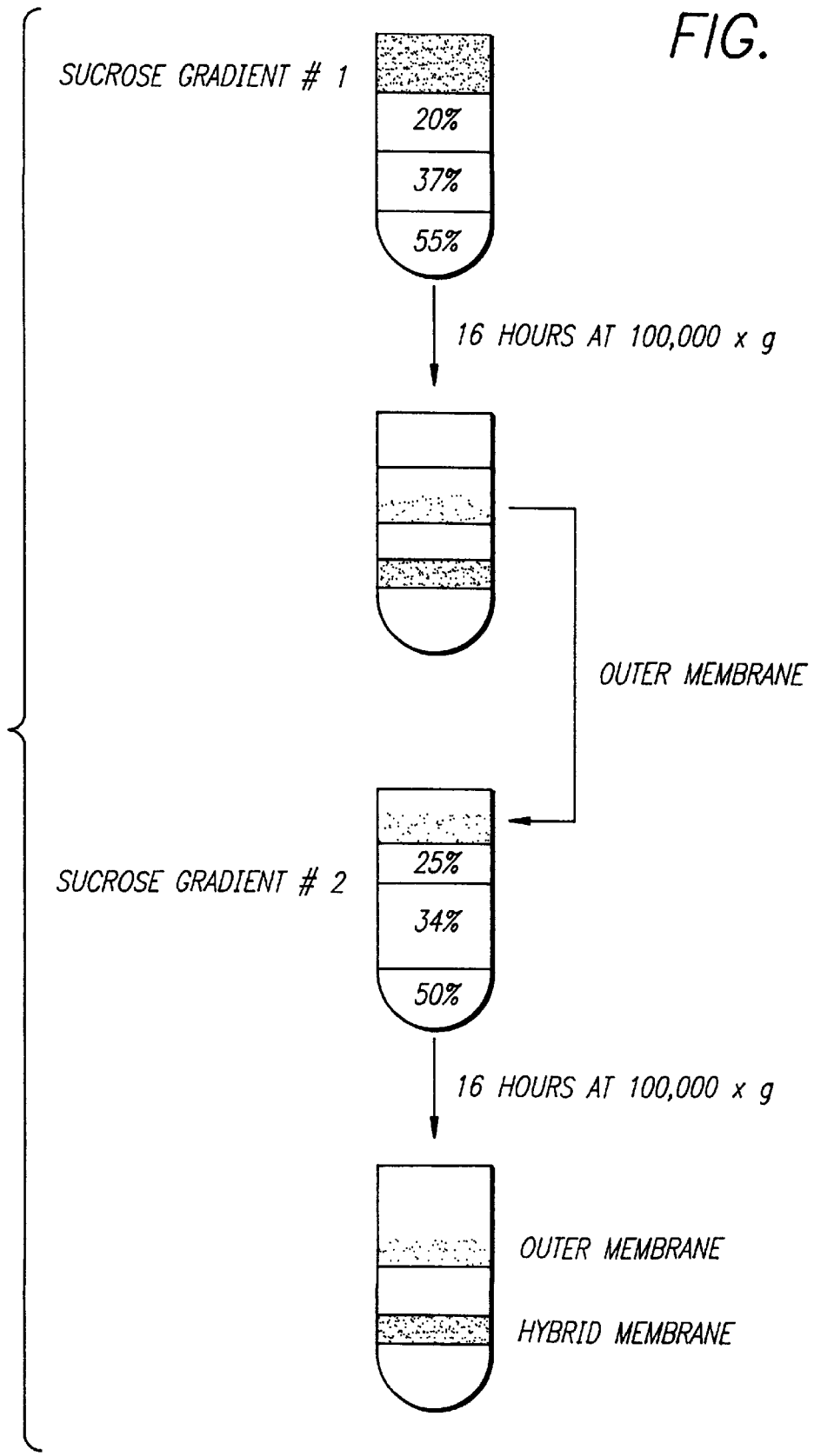
FIG. 9 schematically presents the third isolation method for leptospiral outer membrane.

*Leptospira kirschneri*, strain RM52, was grown to mid log phase (density less than $2 \times 10^8$/ml) in bovine serum albumin Tween-80 medium (bovuminar PLM-5 micorbiological media, Intergen, Purchase, New York). Bacteria were washed once in 0.1 M phosphate-buffered saline, pH 7.4 (PBS) containing 5 mM $MgCl_2$ and resuspended in 10 ml of HNSE buffer [20 mM HEPES, pH 7.6, 1 M NaCl, 10% sucrose (weight/volume), 1 mM EDTA] at 4° C. Bacteria were passed three times through a French pressure cell at 12,000 lb/in². The following were added to the suspension: DNAse (I unit/ml), RNAse (0.25 μg/ml), and egg white lysozyme (500 μg/ml). After incubation at 4° C. for 2 hours, the suspension was passed through a 0.2 micron filter and the outer membrane was isolated by isopycnic ultracentrifugation in two successive steps as shown schematically in FIG. 9. In the first step, the material was layered onto a discontinuous gradient consisting of 5 ml of 55%, 15 ml of 37%, and 10 ml of 20% sucrose in HNE buffer (20 mM HEPES, pH 7.4, 1 M NaCl, 1 mM EDTA). The gradient was placed in a Beckman SW28 rotor and centrifuged (100, 000×g for 16 hr). The material that moved into the 20% pad (enriched outer membrane) was collected and layered onto a second discontinuous gradient consisting of 5 ml of 50%, 16 ml of 34%, and 8 ml of 25% sucrose in HNE buffer. The gradient was placed in Beckman SW28 rotor and centrifuged (100,000×g for 16 hr).

One milliliter fractions were collected from the bottom of each tube. The density of each fraction was estimated by measuring the refractive index with a refractometer. The protein concentration of each fraction was estimated by measuring the $A_{280}$. The fraction were analyzed for protoplasmic cylinder contamination by addition of digoxigenin-ampicllin conjugate for detection of penicillin-binding protein by chemiluminiscence {Weigel, L. M., et al., Antimicrob. Agents Chemother., 38(2): 330–336 (1994)}. Prior to analysis by sodium dodecyl sulfate polyacrylamide gel electrophoresis (SDS-PAGE), samples were precipitated with trichloroacetic acid and solubilized in final sample buffer (FSB) composed of 62.5 mM Tris hydrochloride (pH 6.8), 10% glycerol, 5% 2-mercaptoethanol, and 2% SDS. Proteins were separated on a 12% gel with a discontinuous buffer system {Laemmli, U.K., Nature (London), 227: 680–685 (1970)}, and stained with Coomasie brilliant blue, silver {Wray, W., et al., Anal. Biochem., 118: 197–203 (1981)}, or were transfered to nitrocellulose (Schleicher and Schuell) for immunoblotting. For antigenic detection on immunoblots, the nitrocellulose was blocked with 5% nonfat dry milk in PBS—0.1% Tween-20 (PBS-T), incubated for one hour with primary antisera diluted 1:5000 (unless otherwise noted) in PBS-T, and probed with Donkey anti-rabbit antiserum conjugated to horseradish peroxidase (Amersham). Primary antisera used in this study included rabbit polyclonal antisera specific for the porin OmpL1, the lipoproteins LipL41 and LipL36, and monoclonal antibody F71C21 (gift of R. A. Hartskeerl, Royal Tropical Institute, Amersham) specific for leptospiral LPS. Antigen-antibody binding was detected using the Enhanced Chemiluminescence System (ECL, Amersham). Blots were incubated in ECL reagents for one minute and then exposed to XAR-5 film (Kodak).

RESULTS

Figure 10:
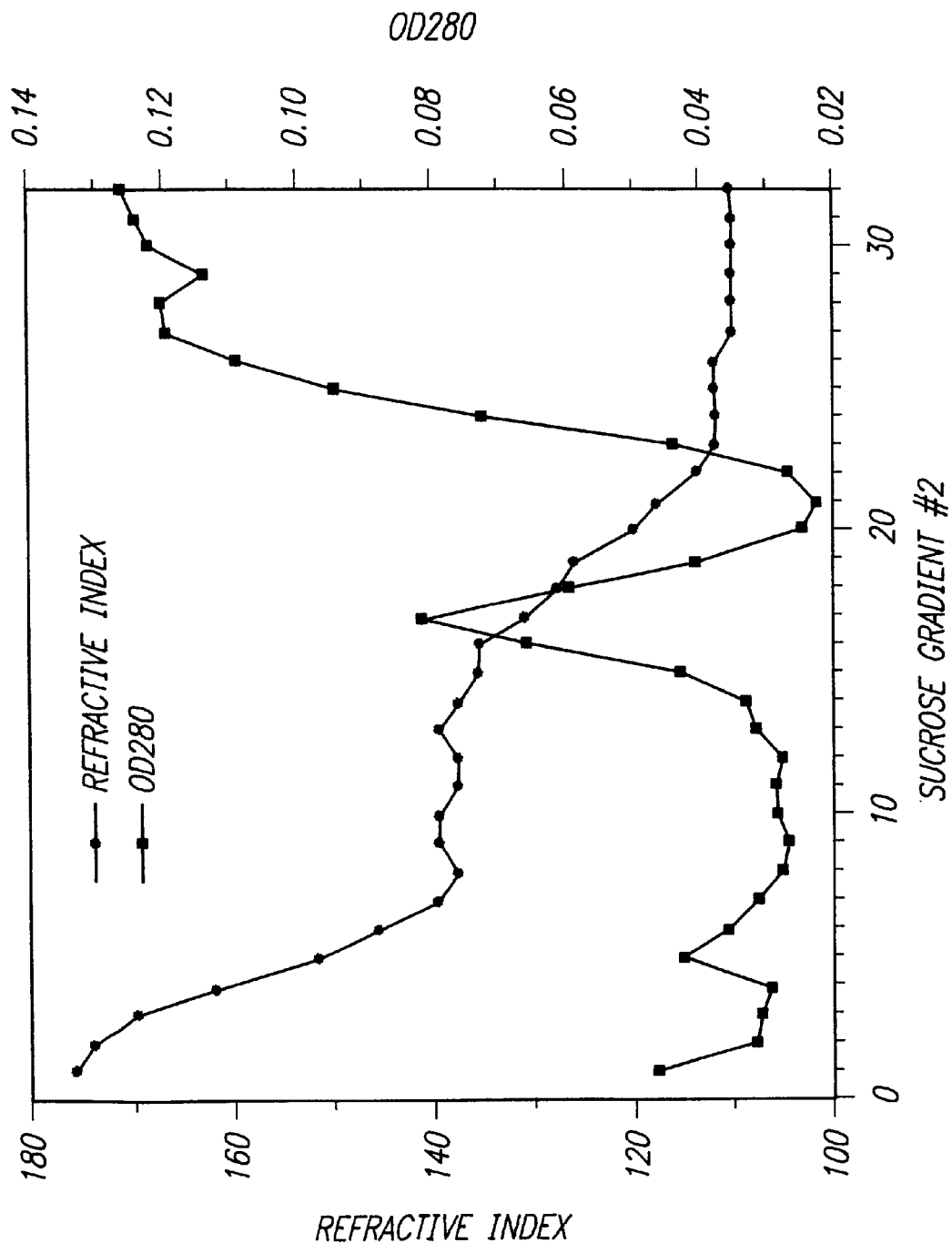
FIG. 10 graphically presents the refractive indices and protein densities of the fractions from the second sucrose gradient.
Figure 11A:
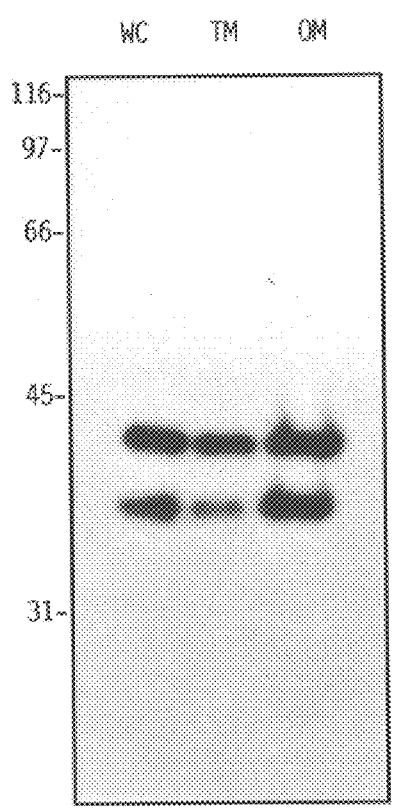
FIG. 11 shows the immunoblots of whole cells (WC), total membrane (TM), and isolated outer membrane (OM) probed with antisera to LipL41 and LipL36 (FIG. 11A), and OmpL1 (FIG. 11B).
FIG. 11C shows the silver stain of SDS-PAGE gel of outer membrane (OM), hybrid membrane (HM), total membrane (TM), and whole cell (WC).
Figure 11B:
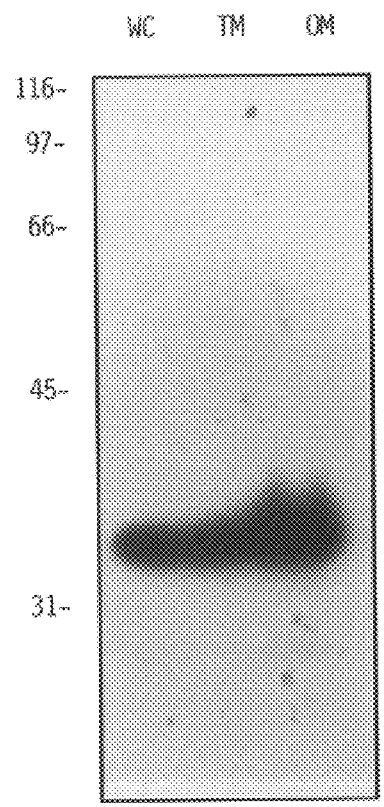
Figure 11C:
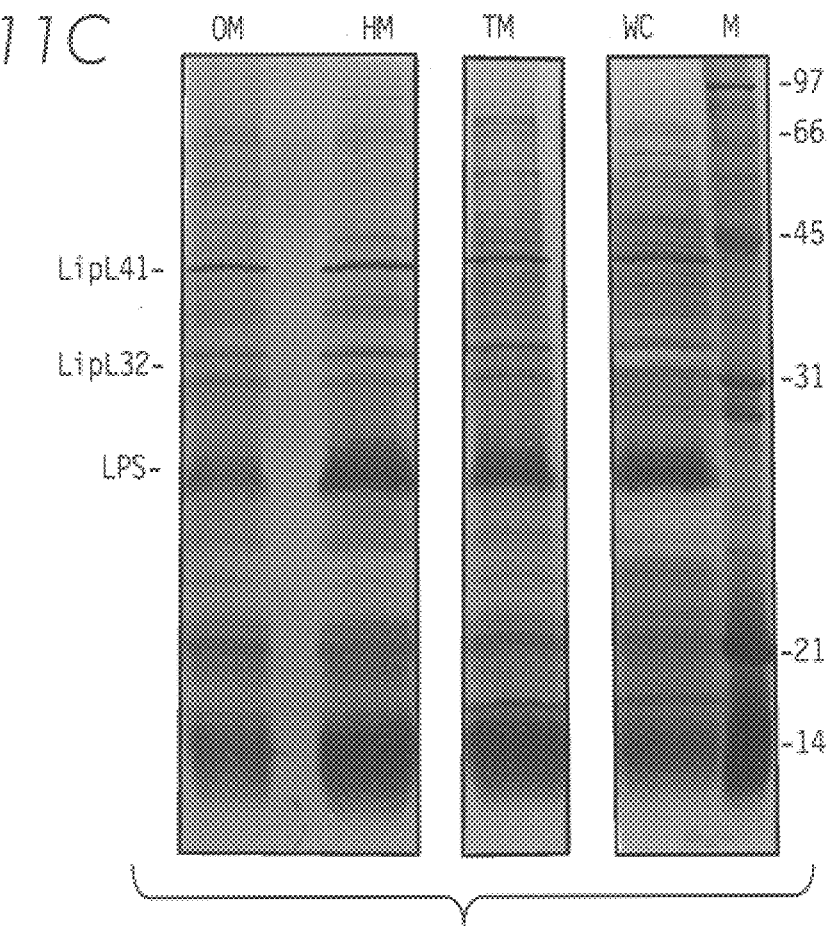

FIG. 10 shows the refractive indices and protein densities of the fraction from the second sucrose gradient. Detection of leptospiral penicdlin-binding proteins by digoxigenin-ampicillin conjugate was ampicillin inhibitable. The outer membrane banded at fraction #17 and was found to contain LipL41 and LipL36 (FIG. 11A), OmpL1 (FIG. 11B), and LPS (data not shown), but was free of contamination by penicillin binding proteins (data not shown), indicating successful separation of the leptospiral outer membrane from protoplasmic cylinder contaminants. The pattern of bands detected using the digoxigenin-ampicillin conjugate was inhibitable by free ampicillin, demonstrating that the detected bands are penicillin-binding proteins. Analysis of the proteins in the isolated outer membrane in fraction #18 by SDS-PAGE and silver stain revealed known outer membrane protein including LipL32 (MOMP), LipL36, and LipL41. The isolated outer membrane also included proteins with molecular masses of approximately 22-, 24-, 30-, 37-, 46-, 51-, 56-, 70-, and 74-kDa (FIG. 11C). The 30-kDa protein is new and was not observed using the first two isolation techniques in EXAMPLE 1, above. The 22-kDa protein is hereby identified as LapL22. A minor protein peak at fraction #5 was found to contain LPS and OmpL1 but was also contaminated by penicillin-binding proteins, indicating a hybrid population of outer and inner membrane vesicles.

Example 3

CHARACTERIZATION OF LapL22

LapL22 is a LPS-associated protein of Leptospira species with a molecular mass of 22 kDa. LapL22 was initially identified as a component of the isolated leptospiral outer membrane. The electrophoretic mobility of LapL22 was also noted to be modifiable by heat, an exclusive property of integral outer membrane proteins with beta-sheet structure. Shang, E. S. et al., Infect. Immun. 63(8): 3174–81 (1995). The following experiment examined the humoral immune response to L. kirschneri infection in the hamster model of leptospirosis and showed the association of LapL22 with leptospiral LPS. Surface-exposure of LapL22 is implied by the fact that LPS is found exclusively on the surface of bacterial outer membranes.

Generation of Infection-Derived Antisera

Hamsters in Group One were infected with culture-adapted, virulent L. kirschneri. Ten days after infection, liver tissue from one of the hamsters in Group One was obtained as a source of host-adapted L. kirschneri. The host-adapted L. kirschneri were immediately inoculated into hamsters in Group Two. Hamsters from both groups surviving twenty-eight days after challenge were euthanized and serum harvested for immunoblot studies. In this way, two types of infection-derived antisera were generated:

SCA=Serum from Group One hamsters infected with Culture-Adaped L. kirschneri.

SHA=Serum from Group Two hamsters infected with Host-Adaped L. kirschneri.

Immunoblot Analysis of Leptospiral Proteins

L. kirschneri proteins were separated by SDS-PAGE and probed with SCA and SHA sera. Four of the antigens recognized by these sera have been characterized: (1) The 33-kDa porin, OmpL1; (2) the 36-kDa lipoprotein, LipL36; (3) The 41-kDa lipoprotein, LipL41; and (4) A form of leptospiral LPS which migrates over a broad range from 24–30 kDa apparent molecular mass, designated herein as $LPS^{24-30}$. Serum from Group One hamsters infected with Culture-Adaped L. kirschneri also produce several LPS species {Haake, D. A., et al., Infect. Immun., 59(3): 1131–40 (1991)}. In addition to $LPS^{24-30}$, a smaller form of LPS is produced which migrates at 18–20 kDa apparent molecular mass, herein designated $LPS^{8-20}$.

Figure 12:
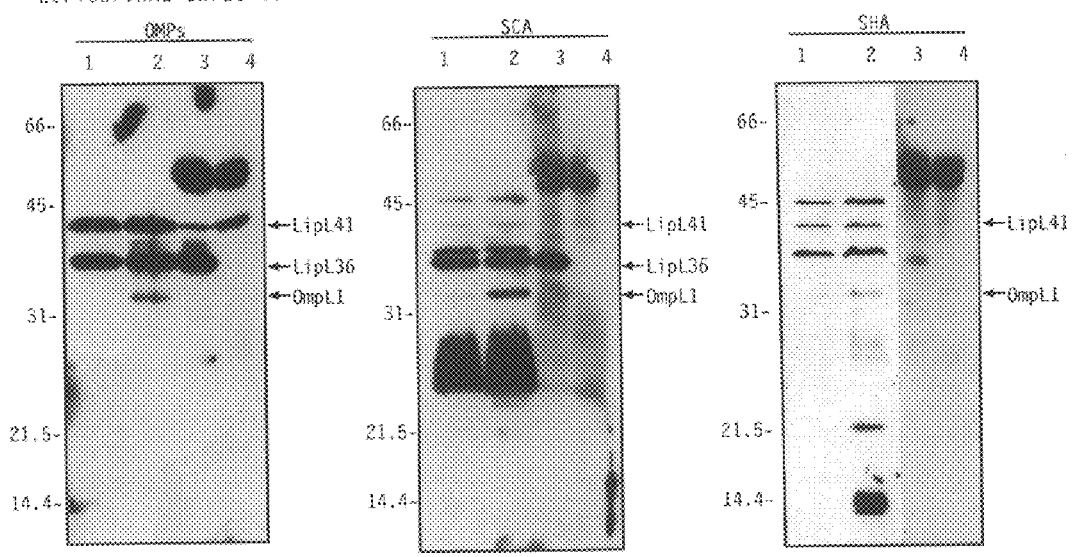
FIG. 12 shows Leptosprial infection results in an antibody response to outer membrane proteins. Immunoblots of leptospiral proteins unheated (lanes 1); boiled (lanes 2); and immunoprecipitated with antisera specific for LipL36 (lanes 3) and LipL41 (lanes 4).

As shown in FIG. 12, SCA immunoblots reacted with leptospiral $LPS^{24-30}$, heat modifiable OmpL1, and non-heat-modifiable proteins LipL36, LipL41, and two additional proteins with molecular masses of 37-, and 46-kDa. SHA sera also reacted with OmpL1, LipL41, and the 37-. And 46-kDa proteins. However, SHA sera reacted more strongly than SCA sera with heat-modifiable proteins with molecular masses of 14-, 22kDa, and less strongly with leptospiral $LPS^{24-30}$ and the 36-kDa protein. Hamster sera from uninfected littermates was nonreactive (data not shown).

Figure 13:
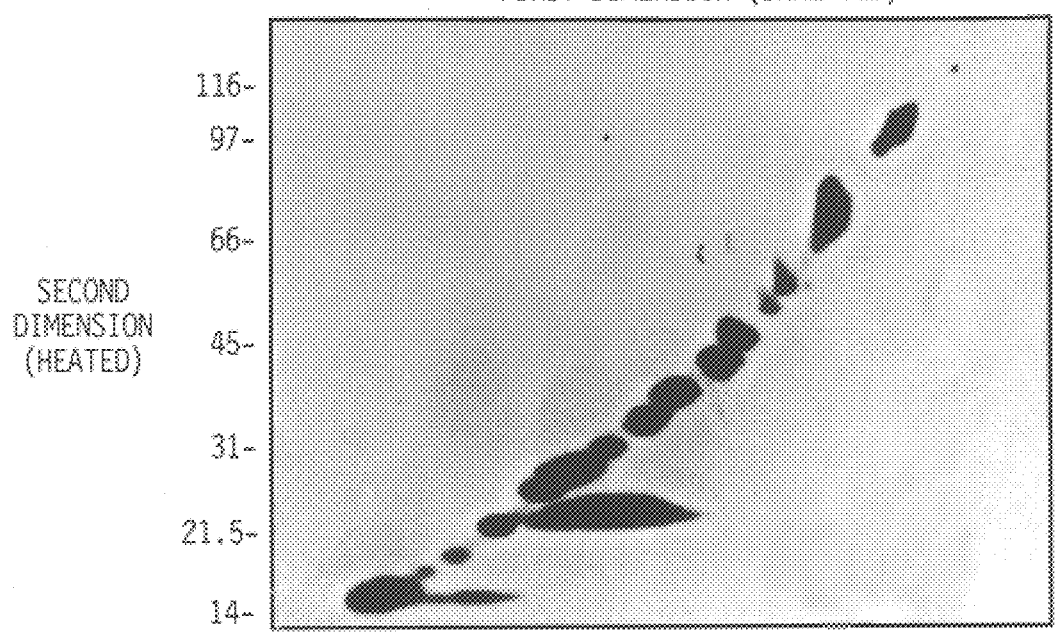
FIG. 13 presents a two-dimensional immunoblot using infection-derived antisera.

SHA antisera was used to probe immunoblots of two-dimensional SDS-PAGE gels in order to determine the migration of the 14-, and 22-kDa heat-modifiable proteins in unboiled samples. As shown in FIG. 13, the 14-kDa protein migrates with an apparent molecular mass of 18–20 kDa in unboiled samples, while the 22-kDa protein migrates with an apparent molecular mass of 24–30 kDa in unbolied samples. This experiment indicates that the 14- and 22-kDa proteins are heatmodifiable because they are are associated with LPS[18–20] and LPS[24–30], respectively, in unboiled samples. This protein-LPS association is stable in sodium dodecyl sulfate at room temperature, but is lost after boiling, presumably due to denaturation of LapL22.

The foregoing is meant to illustrate, but not to limit, the scope of the invention. Indeed, those of ordinary skill in the art can readily envision and produce further embodiments, based on the teachings herein, without undue experimentation.

All publications and patent applications mentioned in this Specification are herein incorporated by reference to the same extent as if each of them had been individually indicated to be incorporated by reference.

I claim:

1. A method of inducing an immune response to a pathogenic spirochete in a subject comprising administering to the subject a pharmaceutical composition containing an immunogenically effective amount of isolated leptospiral outer membrane proteins having molecular masses, as indicated by denaturing polyacrylamide gel electrophoresis, selected from the group consisting of about 70-, about 74-, about 93-, about 101- and about 127-kDa.

2. A method of inducing an immune response to a pathogenic spirochete in a subject comprising administering to the subject a pharmaceutical composition containing an immunogenically effective amount of an isolated leptospiral outer membrane protein having a molecular mass, as indicated by denaturing polyacrylamide gel electrophoresis, of about 93-kDa.

3. A method of inducing an immune response to a pathogenic spirochete in a subject comprising administering to the subject a pharmaceutical composition containing an immunogenically effective amount of an isolated leptospiral outer membrane protein having a molecular mass, as indicated by denaturing polyacrylamide gel electrophoresis, of about 101-kDa.

4. A method of inducing an immune response to a pathogenic spirochete in a subject comprising administering to the subject a pharmaceutical composition containing an immunogenically effective amount of an isolated leptospiral outer membrane protein having a molecular mass, as indicated by denaturing polyacrylamide gel electrophoresis, of about 127-kDa.

5. A method of inducing an immune response to a pathogenic spirochete in a subject comprising administering to the subject a pharmaceutical composition containing an immunogenically effective amount of an isolated leptosprial outer membrane protein having a molecular mass, as indicated by denaturing polyacrylamide gel electrophoresis, of about 74-kDa.

6. The method of claim 1, wherein said pathogenic spirochete is selected from the group consisting of Treponema, Borrelia and Leptospira.

7. The method of claim 1, wherein said protein is in a pharmaceutically acceptable carrier.

8. The method of claim 7, wherein said pharmaceutically acceptable carrier contains an adjuvant.

9. The method of claim 1, wherein the subject is a mammal.

10. The method of claim 9, wherein the mammal is a human.

* * * * *

UNITED STATES PATENT AND TRADEMARK OFFICE
CERTIFICATE OF CORRECTION

PATENT NO. : 5,989,547 Page 1 of 1
DATED : November 23, 1999
INVENTOR(S) : Haake It is certified that error appears in the above-identified patent and that said Letters Patent is hereby corrected as shown below:

Column 1,
Line 9, in the "Government Interests" section after the sentence reading, "This invention was made with Government support through funding from the Veterans' Administration Medical Research Funds," but before the sentence reading " The Government has certain rights in this invention," please insert the following:

-- This invention was made with government support under Contract No. AI 34431 awarded by the National Institutes of Health. --

Signed and Sealed this

Fourth Day of June, 2002

*Attest:*

JAMES E. ROGAN
*Attesting Officer* *Director of the United States Patent and Trademark Office*